United States Patent
Knight

(10) Patent No.: US 10,343,127 B2
(45) Date of Patent: Jul. 9, 2019

(54) EVAPORATION-CONTROLLING CONTAINER INSERTS

(71) Applicant: GEN-PROBE INCORPORATED, San Diego, CA (US)

(72) Inventor: Byron J. Knight, San Diego, CA (US)

(73) Assignee: Gen-Probe Incorporated, San Diego, CA (US)

(*) Notice: Subject to any disclaimer, the term of this patent is extended or adjusted under 35 U.S.C. 154(b) by 492 days.

(21) Appl. No.: 15/002,664

(22) Filed: Jan. 21, 2016

(65) Prior Publication Data

US 2016/0136600 A1 May 19, 2016

Related U.S. Application Data

(62) Division of application No. 14/211,668, filed on Mar. 14, 2014.

(Continued)

(51) Int. Cl.
*B01F 15/00* (2006.01)
*B01F 9/00* (2006.01)
(Continued)

(52) U.S. Cl.
CPC ...... *B01F 15/00837* (2013.01); *B01F 9/0016* (2013.01); *B01F 9/22* (2013.01);
(Continued)

(58) Field of Classification Search
CPC ............... B01L 3/523; B01L 2200/026; B01L 2200/142; B01F 15/00837; B01F 9/0016;
(Continued)

(56) References Cited

U.S. PATENT DOCUMENTS 3,341,979 A 9/1967 Davidson et al.
4,699,767 A 10/1987 Aihara
(Continued)

FOREIGN PATENT DOCUMENTS

DE 9312016 U1 10/1993
DE 19536789 A1 4/1997
(Continued)

OTHER PUBLICATIONS

International Search Report and Written Opinion issued in PCT/US2014/029161, 15 pages (dated Oct. 31, 2014).
(Continued)

*Primary Examiner* — Anshu Bhatia
(74) *Attorney, Agent, or Firm* — Rothwell, Figg, Ernst & Manbeck, P.C.; Charles B. Cappellari

(57) ABSTRACT

An apparatus configured for mixing the contents of one or more fluid containers includes a fluid container support platform configured to hold one or more fluid containers. The fluid container support platform is configured to index the container to one or more specified locations and to be moved in an orbital path about an orbital center independently of the rotation about the central axis of rotation. The apparatus further includes an indexing drive system configured to effect indexing movement of the container support platform and a vortex drive system configured to effect powered orbital movement of the container support platform about the orbital center. An evaporation limiting insert placed within containers reduces exposure of the fluid contents of the container to atmospheric air, thereby reducing susceptibility of the fluid contents to evaporation.

18 Claims, 15 Drawing Sheets

Related U.S. Application Data

(60) Provisional application No. 61/783,670, filed on Mar. 14, 2013.

(51) Int. Cl.
  *B65D 23/00* (2006.01)
  *B01F 9/22* (2006.01)
  *B01F 11/00* (2006.01)
  *B01L 3/00* (2006.01)
  *G01N 35/00* (2006.01)

(52) U.S. Cl.
  CPC ............ *B01F 11/0014* (2013.01); *B01L 3/523* (2013.01); *B65D 23/00* (2013.01); *B01L 2200/026* (2013.01); *B01L 2200/142* (2013.01); *G01N 2035/00524* (2013.01)

(58) Field of Classification Search
  CPC ........ B01F 9/22; B01F 11/0014; B65D 23/00; G01N 2035/00524
  See application file for complete search history.

(56) References Cited

U.S. PATENT DOCUMENTS

| | | | |
|---|---|---|---|
| 5,066,135 A | 11/1991 | Meyer et al. | |
| 5,102,631 A * | 4/1992 | Jordan | B01L 3/508 206/814 |
| 5,167,448 A | 12/1992 | Herold et al. | |
| 5,234,809 A | 8/1993 | Boom et al. | |
| 5,741,708 A | 4/1998 | Carey et al. | |
| 6,534,273 B2 | 3/2003 | Weisburg et al. | |
| 6,666,757 B1 | 12/2003 | Kim | |
| 6,914,555 B2 | 7/2005 | Lipscomb et al. | |
| 7,135,145 B2 | 11/2006 | Ammann et al. | |
| 7,638,337 B2 | 12/2009 | Ammann et al. | |
| 7,666,602 B2 | 2/2010 | Ammann et al. | |
| 7,666,681 B2 | 2/2010 | Ammann et al. | |
| 2006/0178093 A1 | 8/2006 | Hoffman | |
| 2009/0035825 A1 | 2/2009 | Kotler et al. | |
| 2009/0193880 A1 * | 8/2009 | Halverson | B01F 15/00837 73/64.56 |
| 2011/0286298 A1 | 11/2011 | Zamirowski et al. | |
| 2011/0293478 A1 | 12/2011 | Robert et al. | |

FOREIGN PATENT DOCUMENTS

| | | |
|---|---|---|
| EP | 0356883 A1 | 3/1990 |
| EP | 0853495 B1 | 11/2000 |
| GB | 2081118 A | 2/1982 |
| JP | H0280960 A | 3/1990 |
| JP | 02-210266 A | 8/1990 |
| JP | 05-057163 A | 3/1993 |
| JP | 08-052336 A | 2/1996 |
| JP | 2010158203 A | 7/2010 |
| WO | 99/51561 A2 | 11/1999 |
| WO | 99/57561 A2 | 11/1999 |

OTHER PUBLICATIONS

Examination Report No. 1 issued in Australian Patent Application No. 2013202782, 4 pages (dated Jan. 21, 2014).
Office Action issued in Canadian Patent Application No. 2,903,098, 2pages (dated Dec. 8, 2015).
Non-final Office Action issued in U.S. Appl. No. 14/211,056, 30 pages (dated Mar. 14, 2014).
USPTO Final Office Action, U.S. Appl. No. 14/211,668, dated Dec. 16, 2016.
SIPO Search Report, Chinese Application No. 201480015134.9, dated Apr. 25, 2017.
EPO Extended European Search Report, European Patent Application No. 17153490.2, dated May 23, 2017.
USPTO Non-Final Office Action, U.S. Appl. No. 14/211,668, dated Mar. 24, 2017.
EPO Extended European Search Report, European Patent Application No. 17153489.4, dated Jun. 27, 2017.
APO, Examination Report No. 1, Australian Patent Application No. 2017200466, dated Oct. 31, 2018.
EPO, Communication pursuant to Article 94(3) EPC, European Application No. 17153490.2, dated Sep. 27, 2018.
JPO Final Office Action, Japan Patent Application No. 2016-252549, dated Feb. 26, 2019.

* cited by examiner

EVAPORATION-CONTROLLING CONTAINER INSERTS

CROSS REFERENCE TO RELATED APPLICATION

This application claims the benefit under 35 U.S.C. §§ 120, 121 of the filing date of non-provisional patent application Ser. No. 14/211,668 filed Mar. 14, 2014, which claims the benefit under 35 U.S.C. § 119(e) of the filing date of U.S. Provisional Application No. 61/783,670, filed Mar. 14, 2013, which is incorporated herein by reference.

FIELD

This disclosure is directed to a fluid container mixing apparatus configured to carry and agitate a plurality of fluid containers and, in particular, is directed to an apparatus configured to independently move the containers to selectively present any of the containers in a specified location or oscillate the containers in a vortexing motion to agitate the containers and mix the contents thereof.

BACKGROUND

Automated processes, such as chemical, biological, or industrial processes, often involve the use, processing, and/or manipulation of fluid solutions and/or fluid suspensions. Typically, such fluid solutions and suspensions are contained in a plurality of containers, often of various sizes, that must be made accessible to modules of a multi-module instrument for performing such automated processes. In addition, it is often necessary for an operator to provide new, full containers to such an instrument and to remove used, empty containers from the instrument. Thus, it is often necessary in such automated processes to move multiple containers of various sizes to different positions that are accessible to different modules, and/or it is necessary to move different bottles, one-at-a-time, to a single location that is accessible to a particular module.

For example, in a processing instrument that includes a robotic pipettor for aspirating fluids from and/or dispensing fluids into containers, there may be a single location at which fluid containers are accessible to the pipettor, either due to limitations in the movement of the pipettor or due to the fact that other locations are occupied by other modules. It may also be necessary to move bottles from a position at which an operator provides bottles to the instrument to a position within the instrument or to move empty bottles from a position within the instrument to a position where the empty containers can be removed by the operator. Thus, an apparatus is required to move fluid containers from one location within the instrument to one or more other locations within the instrument.

Furthermore, fluid solutions or suspensions must be mixed to maintain the solute in solution or to maintain material, e.g., solid or semi-solid particles, in suspension. Mixing is often effected by agitating the container to mix the fluid solution or fluid suspension contents of the container. Thus, an apparatus is required to agitate the fluid containers. The frequency of mixing required will depend on the nature of the solution or suspension; some solutions or suspensions will require only infrequent mixing while other solutions or suspensions will require constant or nearly constant mixing.

For example, in many nucleic acid diagnostic tests, in which a goal of the test is to identify the presence and/or amount of a nucleic acid of interest, it is well known to use a probe that will hybridize to the nucleic acid of interest and emit, under specified conditions, a detectable signal so as to indicate the presence or, depending on the strength of the signal, the amount of the target nucleic acid that is present in a sample.

Before or after exposing the target nucleic acid to a probe, in certain assays the target nucleic acid can be immobilized by target-capture means, either directly or indirectly, using a "capture probe" bound to a substrate, such as a magnetic bead, or particle. When magnetic beads comprise capture probes, magnets in close proximity to the reaction vessel are used to draw and hold the magnetic beads within a specified area in the vessel, or in a fluid transfer apparatus.

Such target capture probes are provided in the form of fluid suspension. A robotic pipettor aspirates a specified amount of the probe from a container positioned in a location that is accessible to the pipettor and the probe is transported to and dispensed into a receptacle vessel that contains, or will contain, other process materials, including sample material. At times during which the pipettor need not access the container, the container should be agitated to maintain the magnetic particles of the probe in suspension if additional aliquots of the fluid suspension are required.

In an instrument for performing automated processes that includes multiple processing modules, it is typically desirable that the instrument occupy as compact a space as possible, and it is indispensable that the various modules be configured and arranged to operate without interfering with each other. Due to space limitations, therefore, it may not be practical to accommodate separate apparatuses for moving and agitating fluid containers. Moreover, if frequent agitation of a container is required to maintain the fluid in solution or suspension, it may be impractical to move containers back and forth between apparatuses for moving the container and agitating the container. Thus, an ideal fluid handling module for an instrument for performing automated processes supports the combined functionalities of moving containers to one or more specified locations within the instrument and agitating the containers in a compact and space-efficient platform.

SUMMARY

Aspects of the present disclosure are embodied in a fluid container mixing apparatus comprising a container support platform, an indexing drive system, and a vortex drive system. The container support platform is configured to hold one or more fluid containers and is constructed and arranged to be movable in such a manner to index the fluid containers to sequentially place each of the containers in one or more predetermined positions, and the container support platform is configured to be movable in an orbital path about an orbital center. The indexing drive system is configured to effect powered indexing movement of the container support platform. The vortex drive system is configured to effect powered movement of the container support platform in the orbital path.

According to other aspects of the disclosure, the container support platform is constructed and arranged to index the fluid containers by rotating about an axis of rotation.

According to other aspects of the disclosure, the indexing drive system is configured to effect powered rotation of the container support platform.

According to other aspects of the disclosure, the indexing drive system and the vortex drive system are configured to be operable independently of each other.

According to other aspects of the disclosure, the indexing drive system and the vortex drive system are configured to be selectively operated simultaneously.

According to other aspects of the disclosure, the indexing drive system comprises a indexing drive motor having a rotating output shaft operatively coupled to the container support platform to convert powered rotation of the output shaft into rotation of the container support platform.

According to other aspects of the disclosure, the indexing drive motor is operatively coupled to the container support platform by a driveshaft wheel mounted to the output shaft, an indexing drive pulley coupled to the container support platform, and a drive belt trained about the driveshaft wheel and the indexing drive pulley.

According to other aspects of the disclosure, the indexing drive motor is operatively coupled to the container support platform by a driveshaft gear rotated by the output shaft and an indexing drive gear coupled to the container support platform, wherein the driveshaft gear is operatively engaged with the indexing drive gear.

According to other aspects of the disclosure, the vortex drive system comprises a vortex drive motor having an output shaft and a vortex transmission. The vortex transmission is coupled to the vortex drive motor and to the container support platform and is constructed and arranged to convert powered rotation of the output shaft of the vortex drive motor into orbital movement of the container support platform.

According to other aspects of the disclosure, the fluid container mixing apparatus further comprises a driveshaft wheel coupled to the vortex drive motor and a vortex drive belt trained on the driveshaft wheel. The vortex transmission comprises a vortex drive pulley on which the vortex drive belt is trained to transfer rotation of the vortex drive motor to the vortex drive pulley, a vortexing wheel, a shaft rotatably coupling the vortex drive pulley and the vortexing wheel, at least two rotating vortexing elements coupled to the vortexing wheel such that rotation of the vortexing wheel causes a corresponding rotation of the rotating vortexing elements, and an eccentric coupling extending from each of the rotating vortexing elements at a position that is offset with respect to an axis of rotation of the corresponding rotating vortexing element. The container support platform is coupled to the eccentric couplings such that rotation of the vortexing elements imparts powered movement of the container support platform in the orbital path via the eccentric couplings.

According to other aspects of the disclosure, the fluid container mixing apparatus further comprises a counterweight attached to and rotatable with the shaft rotatably coupling the vortex drive pulley and the vortexing wheel.

According to other aspects of the disclosure, each eccentric coupling has the same offset with respect to the axis of rotation of its corresponding rotating vortexing element.

According to other aspects of the disclosure, the vortexing wheel comprises a vortexing pulley, each rotating vortexing element comprises a vortexing idler pulley, and the vortex transmission further comprises a belt coupling the vortexing pulley to the vortexing idler pulleys.

According to other aspects of the disclosure, the fluid container mixing apparatus further comprises one or more belt tensioners configured for adjusting the tension of the belt coupling the vortexing pulley to the vortexing idler pulleys.

According to other aspects of the disclosure, each belt tensioner comprises a slide, a tension wheel rotatably mounted to the slide and bearing against the belt coupling the vortexing pulley to the vortexing idler pulleys, and a tension adjuster screw configured to fix the slide and the tension wheel at a position that provides the desired tension in the belt.

According to other aspects of the disclosure, the vortexing idler pulleys are disposed at a common radial distance from an axis of rotation of the vortexing pulley.

According to other aspects of the disclosure, the vortexing idler pulleys are disposed at equal angular intervals with respect to the vortexing pulley.

According to other aspects of the disclosure, the vortexing wheel comprises a vortexing gear, and the vortex transmission further comprises a gear train associated with each eccentric coupling whereby each rotating vortexing element comprises a gear of the associated gear train. Each gear train is constructed and arranged to rotationally couple each eccentric coupling with the vortexing gear.

According to other aspects of the disclosure, each gear train comprises a transfer gear engaged with the vortexing gear and with the rotating vortexing element.

According to other aspects of the disclosure, the container support platform comprises a turntable and a fluid container tray attached to the turntable.

According to other aspects of the disclosure, the container support platform comprises a plurality of container receptacles, each configured to receive a fluid container.

According to other aspects of the disclosure, the plurality of the container receptacles comprise at least two different sizes.

According to other aspects of the disclosure, each receptacle includes an opening through which a machine-readable code on the fluid container held in the receptacle can be read.

According to other aspects of the disclosure, each container receptacle includes a fluid container retainer element configured to releasably hold a container within the receptacle.

According to other aspects of the disclosure, the fluid container retainer element comprises a resilient element configured to compress when a container is placed into the container receptacle and to resiliently expand to press the container against a wall of the container receptacle.

According to other aspects of the disclosure, the fluid container mixing apparatus further comprises feedback sensors configured to indicate a position or status of at least one of the indexing drive system and the vortex drive system.

According to other aspects of the disclosure, the fluid container mixing apparatus further comprises a machine code reader constructed and arranged to read a machine-readable code on a fluid container carried on the container support platform.

According to other aspects of the disclosure, the machine code reader comprises a bar code reader.

According to other aspects of the disclosure, the machine code reader comprises a radio frequency reader.

According to other aspects of the disclosure, the fluid container mixing apparatus comprises three vortexing elements, each of the rotating vortexing element comprising a vortexing idler pulley. The vortex transmission further comprises a belt coupling the vortexing pulley to two of the vortexing idler pulleys; the apparatus further. The apparatus further includes a first belt tensioner configured to adjust the tension of the belt and located between the vortexing pulley and one of the two vortexing idler pulleys, a second belt tensioner configured to adjust the tension of the belt and located between the vortexing pulley and the other of the two vortexing idler pulleys, and a third belt tensioner configured to adjust the tension of the belt and located between the two vortexing idler pulleys. The first, second, and third belt tensioners are configured to adjust the length of belt between the vortexing pulley and either of the two vortexing idler pulleys and between the two vortexing idler pulleys, to adjust the relative phase of the eccentric couplings associated with the two vortexing idler pulleys.

According to other aspects of the disclosure, the fluid container mixing apparatus further comprises one or more containers supported on the container support platform and including an evaporation-limiting insert comprising a tubular body extending into the container from an opening of the container and having one or more holes formed therein to permit fluid to flow into or out of a space inside the tubular body.

According to other aspects of the disclosure, the evaporation-limiting insert has an irregular bottom edge such that at least a portion of the bottom edge is not perpendicular to a longitudinal axis of the tubular body and whereby a gap is formed between the bottom edge and a bottom surface of the container when the evaporation-limiting insert is fully inserted into the container.

According to other aspects of the disclosure, the evaporation-limiting insert further includes a retainer feature configured to engage a portion of the container to secure the insert within the container.

According to other aspects of the disclosure, the retainer feature comprises a detent configured to engage an inside surface of the container.

According to other aspects of the disclosure, the retainer feature comprises two or more outwardly splayed tabs formed at a top portion of the tubular body and configured to deflect inwardly when the insert is inserted into a container and to press resiliently against an inside surface of the container.

Other aspects of the disclosure are embodied in a method of selectively transporting a plurality of fluid containers or agitating the fluid container to mix the contents of the fluid containers. The method comprises supporting the plurality of fluid containers on a container support platform, moving the container support platform to index the fluid containers by sequentially placing each of the containers in one or more predetermined positions, and agitating the fluid containers to mix the contents of the fluid containers by moving the container support platform in a vortexing motion comprising moving the container support platform in an orbital path about an orbital center, wherein the moving step and the agitating step are performed independently.

According to other aspects of the disclosure, moving the container support platform to index the fluid containers comprises rotating the fluid support about an axis of rotation.

According to other aspects of the disclosure, the method further comprises monitoring a position or status of container support platform during at least one of the moving step and the agitating step.

According to other aspects of the disclosure, each of the plurality of fluid containers contains machine readable identification indicia that is read by a machine code reader during the moving step or while pausing the moving step.

According to other aspects of the disclosure, the method further comprises supporting one or more containers on the container support platform and providing at least one of the containers with an evaporation-limiting insert comprising a tubular body extending into the container from an opening of the container and providing one or more holes in the tubular body to permit fluid to flow into or out of a space inside the tubular body.

According to other aspects of the disclosure, the method further comprises providing the evaporation-limiting insert with an irregular bottom edge such that at least a portion of the bottom edge is not perpendicular to a longitudinal axis of the tubular body and whereby a gap is formed between the bottom edge and a bottom surface of the container when the evaporation-limiting insert is fully inserted into the container.

According to other aspects of the disclosure, the method further comprises providing the evaporation-limiting insert with a retainer feature configured to engage a portion of the container to secure the insert within the container.

Other aspects of the disclosure are embodied in an evaporation-limiting insert for a container comprising a tubular body and an irregular edge at one end of the tubular body. The tubular body extends into the container from an opening of the container and has one or more holes formed therein to permit fluid to flow into or out of a space inside the tubular body. At least a portion of the irregular edge is not perpendicular to a longitudinal axis of the tubular body so that a gap is formed between the irregular edge and a bottom surface of the container when the evaporation-limiting insert is fully inserted into the container.

According to other aspects of the disclosure, the evaporation-limiting insert includes a retainer feature configured to engage a portion of the container to secure the insert within the container.

According to other aspects of the disclosure, the retainer feature comprises a detent configured to engage an inside surface of the container.

According to other aspects of the disclosure, the retainer feature comprises two or more outwardly splayed tabs formed at a top portion of the tubular body and configured to deflect inwardly when the insert is inserted into a container and to press resiliently against an inside surface of the container.

Other features and characteristics of the present disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various, non-limiting embodiments of the present disclosure. In the drawings, common reference numbers indicate identical or functionally similar elements.

DETAILED DESCRIPTION

Figure 1:
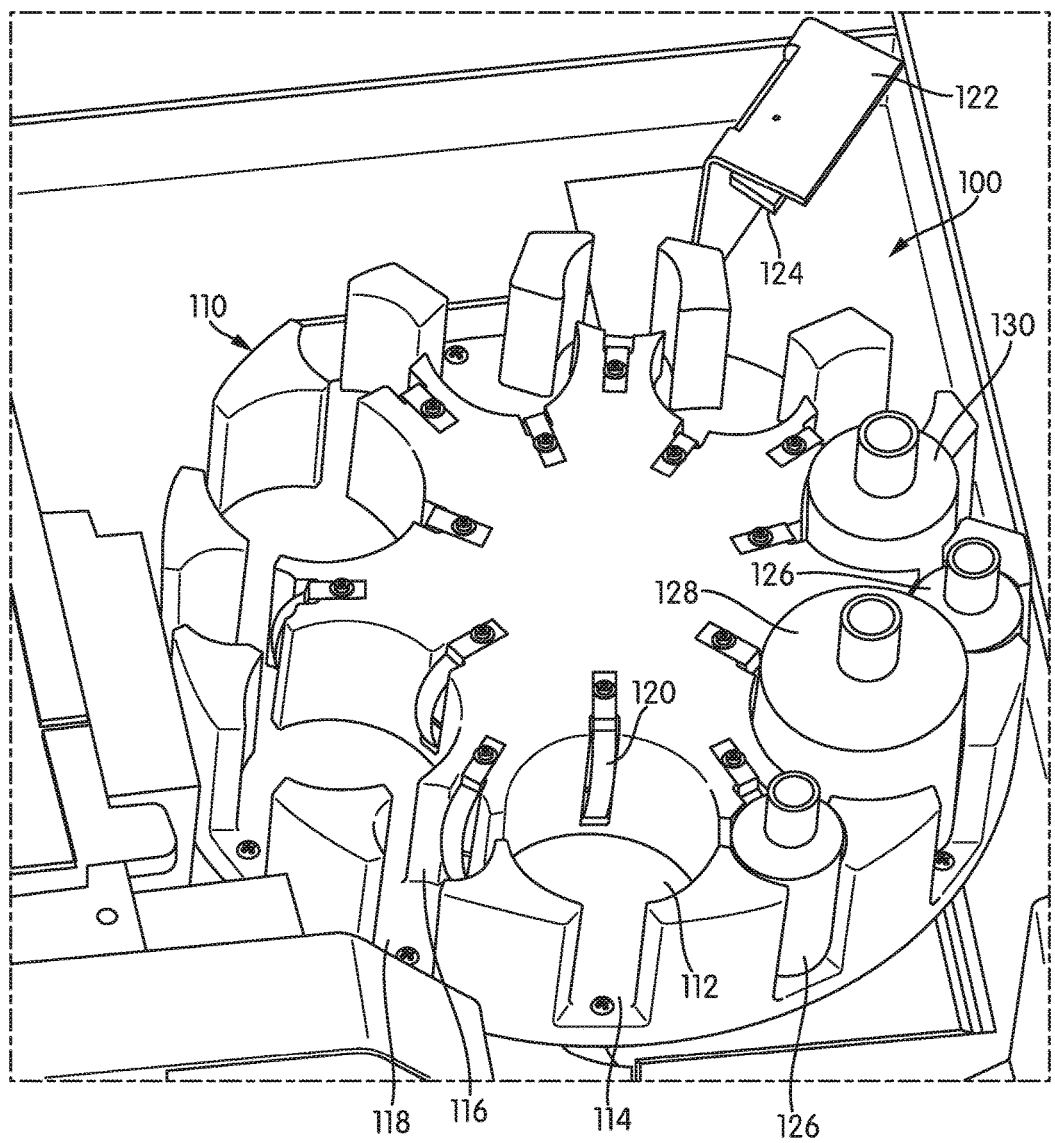
FIG. 1 is a top perspective view of a fluid container mixing apparatus embodying aspects of the present disclosure.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of one component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Figure 2:
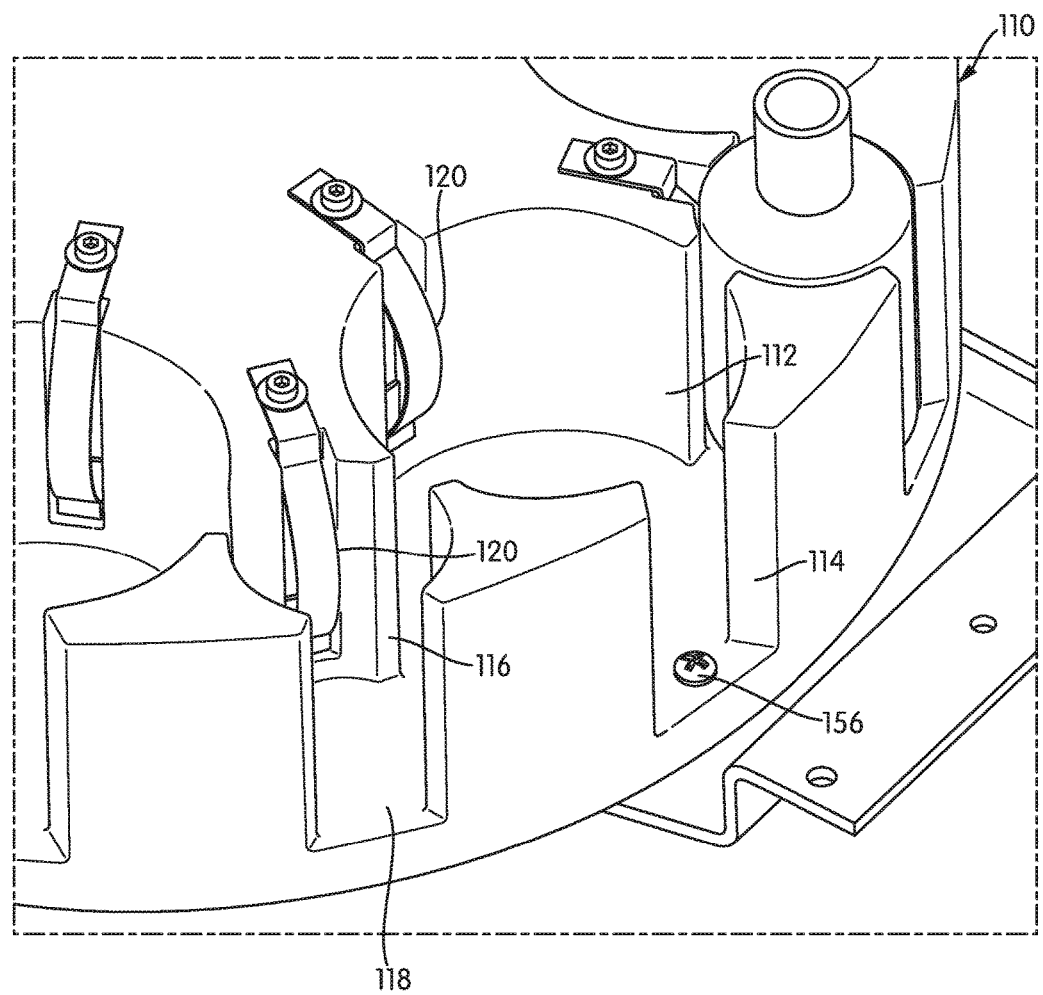
FIG. 2 is a partial enlarged top perspective view of the apparatus.
Figure 3:
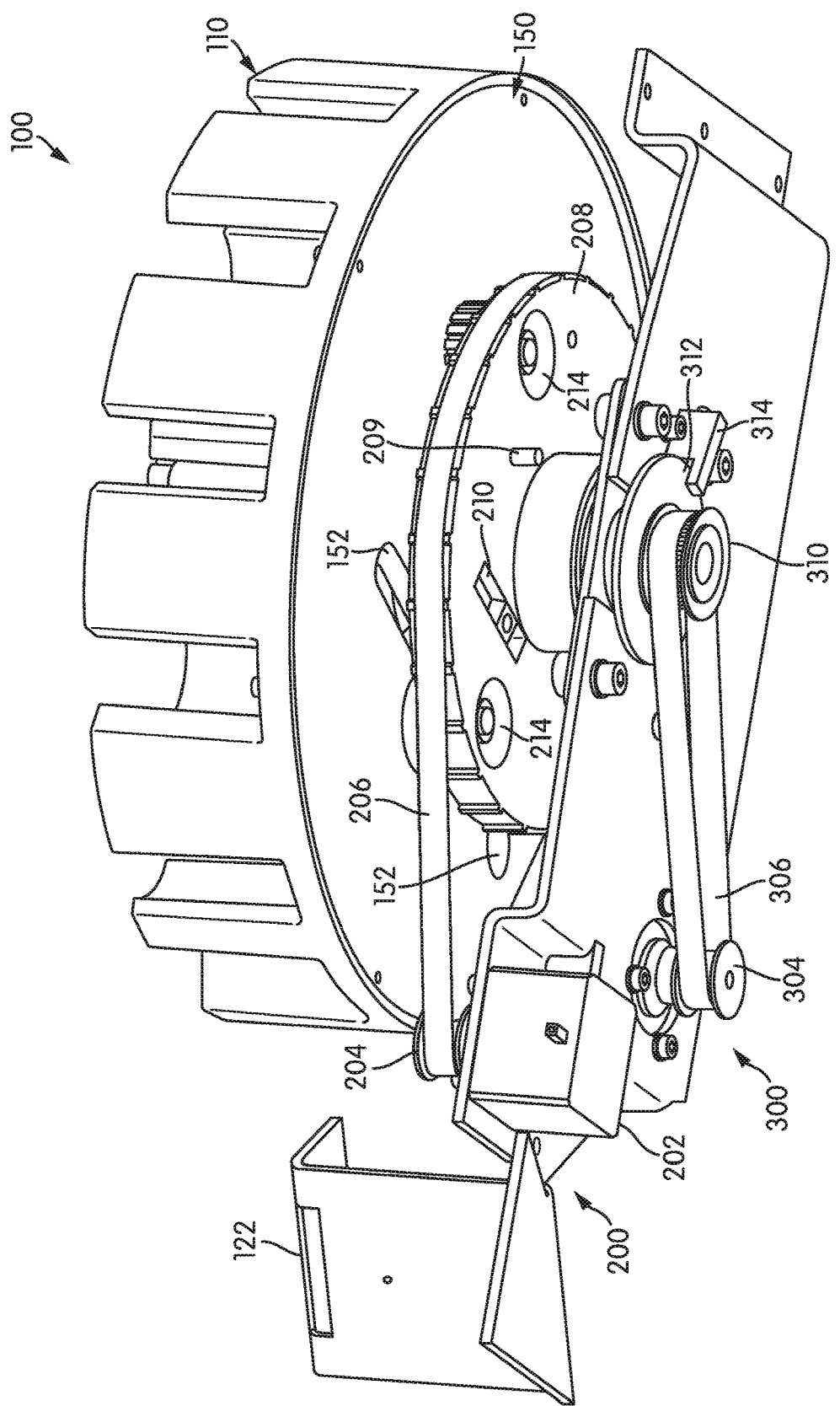
FIG. 3 is a bottom perspective view of the apparatus.

A fluid container mixing apparatus embodying aspects of the present disclosure is indicated by reference number 100 in FIGS. 1, 2, and 3. The apparatus 100 includes a container support platform configured to hold one or more fluid container and to be selectively indexed to present each container to a predetermined position. In the present disclosure "index" or "indexing" the containers refers to moving the containers carried on the fluid container support platform to selectively and sequentially place each of the containers in one or more predetermined positions. In the illustrated embodiment, the container support platform is rotatable about an axis of rotation. In other embodiments, indexing of the containers may comprise moving the containers on one or more carriers moving in a predefined path having a circular, oval or other continuous shape. In the illustrated embodiment, the container support platform comprises a container tray 110, configured to hold a plurality of fluid containers, and a turntable 150 to which the container tray 110 is attached.

The container support platform is also configured to be movable in a vortexing, or orbital path about an orbital center.

Figure 13:
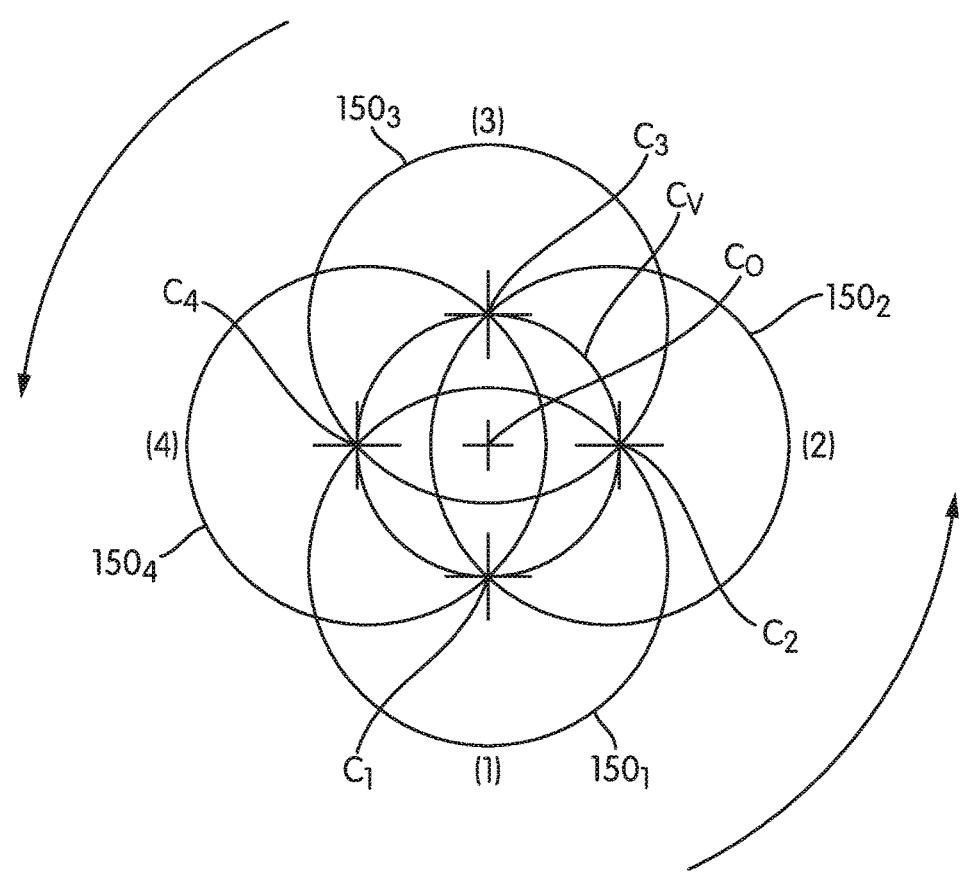
FIG. 13 illustrates the vortex motion of the apparatus.

In the context of the present description, the terms vortex, vortexing, orbit, orbital, or similar terms when used to describe the motion of the fluid container support platform (fluid container tray 110 and turntable 150) refers to a path of motion whereby the entire fluid container support platform moves about an orbital, or vortex, center independently of the indexing of the container support platform (e.g., an rotation or spinning of the fluid container support platform about an axis of rotation of the platform). This is shown in FIG. 13, which illustrates the vortex motion of the turntable 150. During the vortex motion, the turntable 150 is moved such that the center "C" of the turntable 150 orbits about a vortex circle $C_V$ centered at an orbital center $C_O$ through positions $C_1$, $C_2$, $C_3$, $C_4$ as the turntable moves through positions $150_1$, $150_2$, $150_3$, $150_4$.

Apparatus 100 further includes a turntable drive system 200 coupled to the fluid container support platform and constructed and arranged to effect powered indexing of the fluid container support platform. In the illustrated embodiment, the turntable drive system 200 effects powered rotation of the fluid container support platform about its axis of rotation. Apparatus 100 further includes a vortex drive system 300 coupled to the fluid container support platform and configured to effect vortexing, orbital movement of the fluid container support platform bout its orbital center.

The turntable drive system 200 and the vortex drive system 300, in one embodiment, are independent of each other such that the container tray and turntable can be independently indexed (e.g., rotated about a central rotational axis) or vortexed about a plurality of vortex axes. The turntable drive system 200 and the vortex drive system 300 may also operate simultaneously to simultaneously rotate and vortex the container tray, which may facilitate improved mixing of the contents of the containers.

As shown in FIGS. 1 and 2 the container tray 110 includes a plurality of cup-like, generally cylindrical container receptacles and may include container receptacles of varying sizes, such as larger container receptacles 112 and smaller container receptacles 116, configured to receive and hold fluid containers (e.g., bottles) 126, 128, 130 of varying sizes. In addition, to accommodate different container sizes, separate drop-in adapters may be provided for the receptacles 112, 116. The adaptor will permit the introduction and fixed placement of fluid containers in receptacles 112, 116 that have diameters that are smaller than the diameter of receptacles 112, 116. The container tray 110 is preferably circular in shape, and the container receptacles 112, 116, are preferably symmetrically disposed about a central axis of the container tray 110. In the illustrated embodiment, container receptacles 112 include outwardly facing openings 114, and container receptacles 116 include outwardly facing openings 118. The openings 114, 118 are configured to enable a machine code reader 124 mounted on a machine code reader bracket 122 to read a machine code disposed on a container and aligned with the opening 114 or 118. Machine code reader 124 may be a barcode reader configured to read one-dimensional and/or two-dimensional barcodes formed on labels placed on the containers 126, 128, 130 placed in the container receptacles 112, 116. Other machine code reader devices are contemplated, such as radio frequency identification. Each container receptacle 112, 116 may include a receptacle-empty label that is read by the reader 124 when no container is held in the associated receptacle.

Container tray 110 may be formed of any suitable material, and, in one example, it is formed of molded plastic.

The container tray 110 further includes a container retainer element 120 disposed in each container receptacle 112, 116. The retainer element 120 may be a resilient element configured to compress when a container is placed into the container receptacle and to resiliently expand to press the container against a wall of the container receptacle. In the illustrated embodiment, the container retainer element 120 comprises a spring clip 120 formed by a bowed strip of spring steel and attached to the container tray 110 at a radially inward portion of each container receptacle 112, 116. Alternatively, the spring clip may be fabricated from injection molded plastic, rather than bent metal. As will be appreciated by persons of ordinary skill in the art, the container retainer element 120 is configured to flex inwardly when an appropriately-sized container is placed in the container receptacle 112 or 116, and the resilience of the retainer element 120 will urge the container radially outwardly toward the opening 114 or 118 of the respective container receptacle 112 or 116. One purpose of the retainer element 120 is to prevent the containers from rotating within their respective container receptacle 112 or 116 (which would misalign the barcode label and prevent reading) and to prevent containers from rattling loosely in their respective container receptacle 112 or 116. The retainer element 120 may be configured to accommodate containers of different sizes. As shown in FIG. 1, containers 128 and 130 are of different sizes and are both held in a "large" receptacle 112. The spring clip 120 shown in FIG. 1 can compress to a large extent to accommodate the larger container 128 and can compresses to a lesser extent and can expand to securely hold the smaller container 130 within the relatively oversized receptacle 112.

Figure 6:
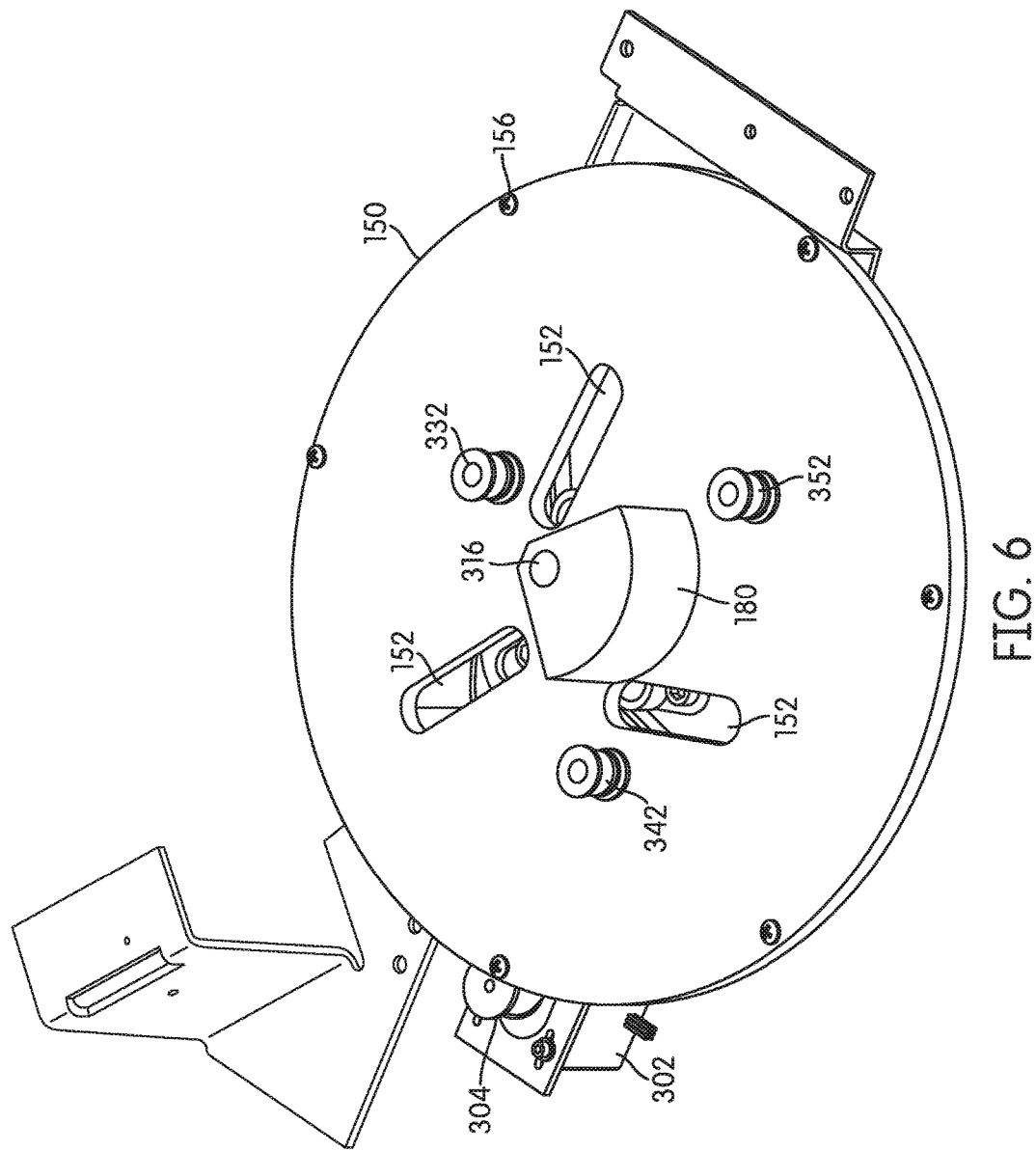
FIG. 6 is a top perspective view of the apparatus with the container tray removed and showing the turntable of the apparatus.

As shown in FIGS. 3 and 6, the turntable 150 comprises a disk may be circular in shape and is configured to be rotatable about a central axis thereof. In other embodiments, the turntable has other shape and each is configured to be rotatable about an axis that is generally perpendicular to the plane of the turntable. Turntable 150 may be formed from any suitable material having sufficient strength, rigidity, and machinability that is preferably, in certain embodiments, lightweight. Suitable exemplary materials include aluminum, stainless steel, or a variety of known engineering plastics.

Three slots 152 are formed through the turntable 150. The turntable 150 is further engaged by three eccentric couplings 342, 352, 362 extending through corresponding openings formed in the turntable 150. A wedge-shaped counterweight 180 is disposed on a shaft 316 extending axially through the turntable 150. Further details regarding the construction and functionality of the slots 152, eccentric couplings 342, 352, 362, counterweight 180, and shaft 316 will be described below.

As shown in FIGS. 2 and 6, the container tray 110 may be secured to the turntable 150 by any suitable means, including mechanical fasteners, such as screws 156, extending through the container tray 110 and into screw-receiving openings formed about the perimeter of the turntable 150.

Figure 4:
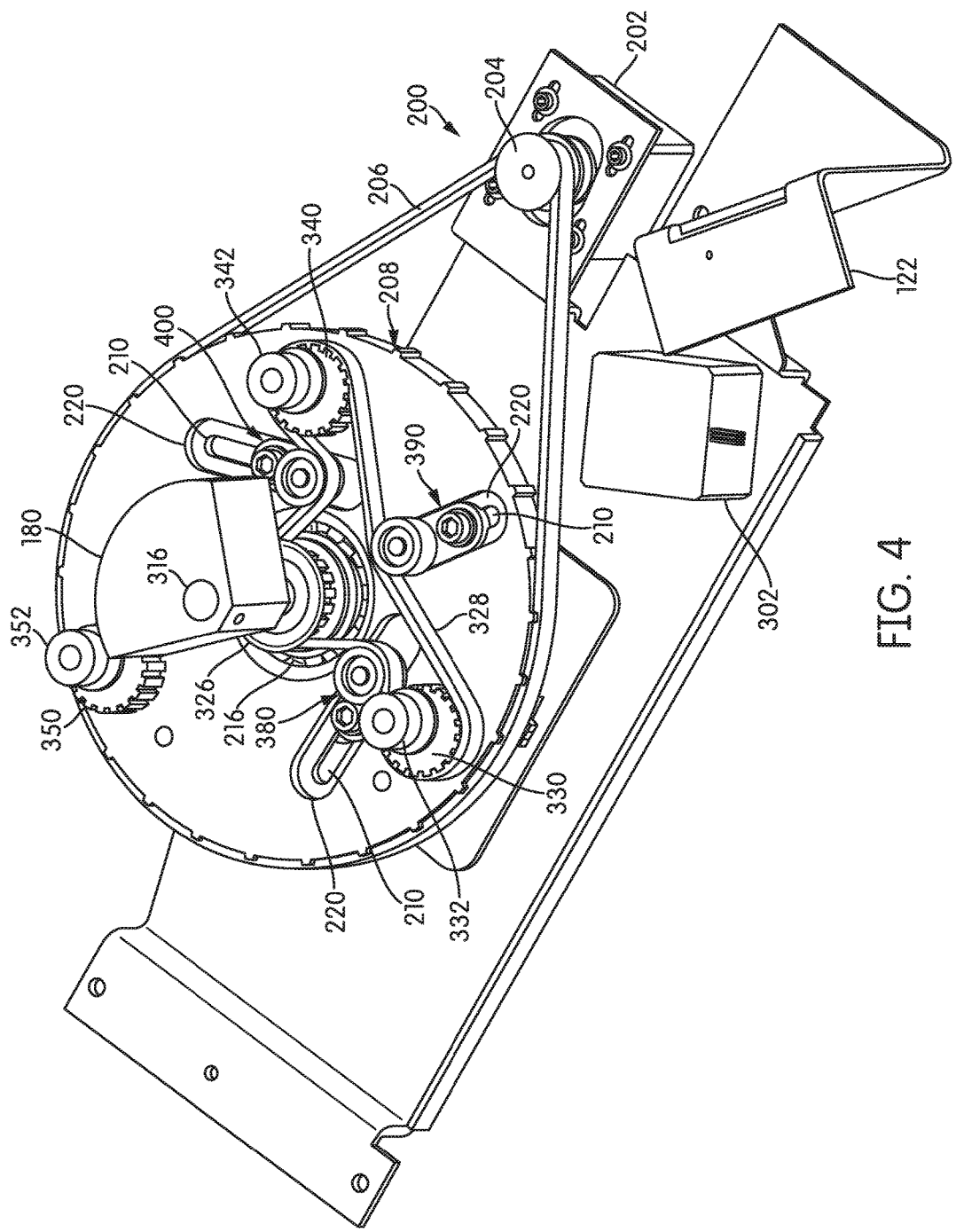
FIG. 4 is a top perspective view of the apparatus with a container tray and turntable of the apparatus removed.
Figure 5:
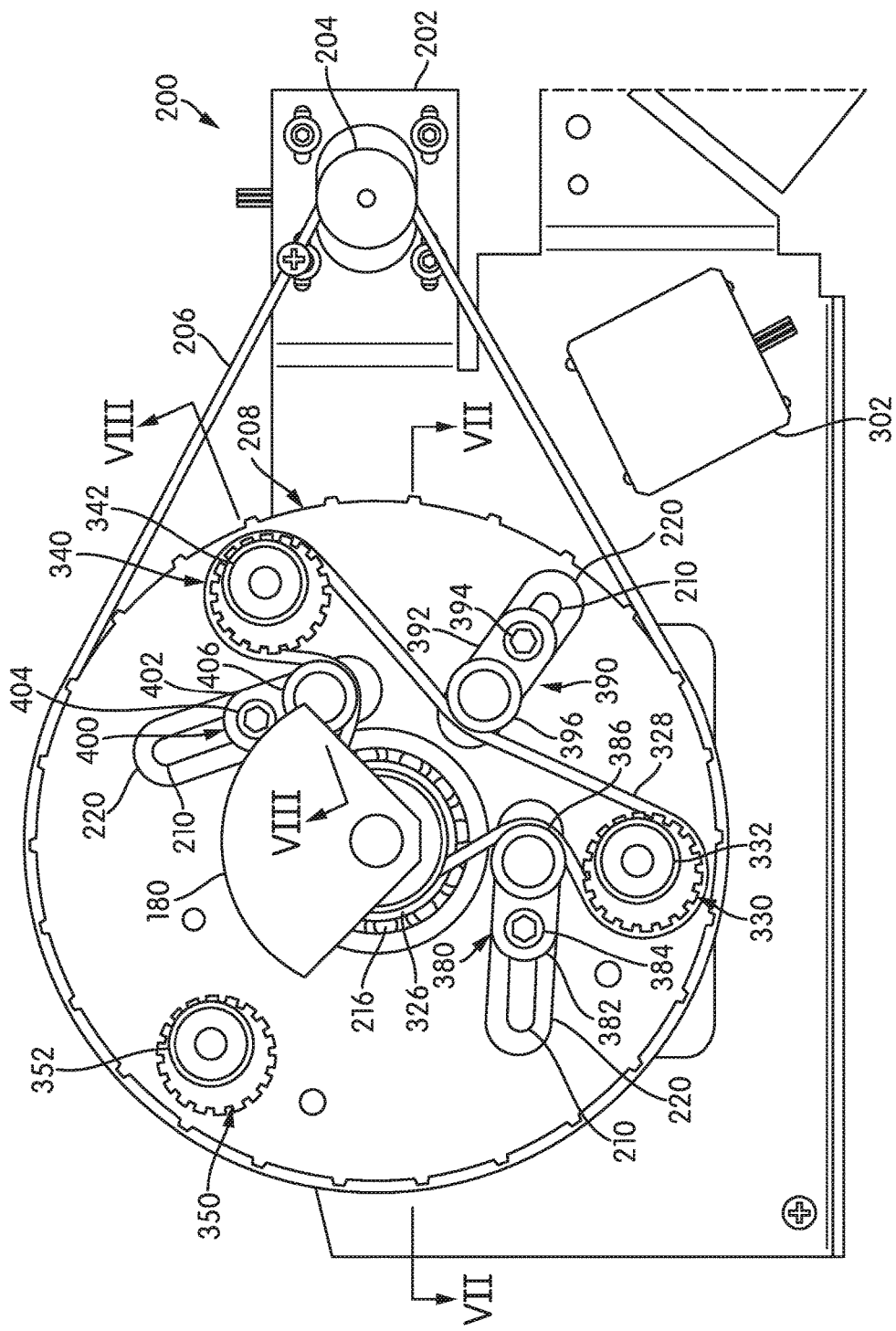
FIG. 5 is a top plan view of the apparatus with the container tray and turntable removed.

Details of an exemplary turntable drive system 200 are shown in FIGS. 3, 4 and 5. The turntable drive system 200 includes a turntable drive motor 202 coupled to the container support platform. In the illustrated embodiment, the turntable drive motor 202 has a driveshaft wheel 204 attached to an output shaft of the motor 202. A rotatable turntable drive pulley 208 is coupled to the turntable 150. A turntable drive belt 206 extends over the drive shaft wheel 204 of the turntable drive motor 202 and the turntable drive pulley 208 such that rotation of the driveshaft wheel 204 by the turntable drive motor 202 effects powered rotation, via the turntable drive belt 206, of the turntable drive pulley 208 and the turntable 150.

Turntable drive motor 202 is preferably a stepper motor and may include a rotary encoder for controlling and monitoring the rotational position of the motor 202 and the turntable drive pulley 208 and turntable 150 rotated thereby. Turntable pulley 208 may include a rotational feedback sensor, such as a home flag. In the illustrated embodiment, a coupling 209 projects down from the turntable pulley 208 (see FIG. 3), and coupling 209 may be detected by a home flag sensor (e.g., a slotted optical sensor) (not shown) mounted beneath pulley 208. Other types of sensors may be used for indicating a home position. Such sensors may comprise proximity sensors, magnetic sensors, capacitive sensors, etc.

Details of a vortex drive system 300 are shown in FIGS. 3, 4, 5, 7 and 8. As shown in FIGS. 3 and 4, the vortex drive system 300 includes a vortex drive motor 302 coupled to the container support platform. In the illustrated embodiment, the vortex drive motor 302 has a driveshaft wheel 304. A vortex drive belt 306 couples the driveshaft wheel 304 of the vortex drive motor 302 to a vortex transmission 308. Alternatively, the vortex drive motor 302 may be coupled to the vortex transmission by one or more gears or other means known to those of ordinary skill for coupling motor power. The vortex transmission is coupled to the vortex drive motor 302 and to the fluid container support platform (fluid container tray 110 and turntable 150 in the illustrated embodiment) and is constructed and arranged to convert powered rotation of the output shaft of the vortex drive motor 302 into orbital movement of the fluid container support platform.

In the illustrated embodiment, the vortex transmission 308 includes a vortex drive pulley 310 around which the vortex drive belt 306 is trained. The vortex drive pulley 310 is attached to a shaft 316 that is rotatably mounted within shaft bearing 318. Shaft bearing 318 includes a cylindrical housing 320 and a bearing mounting flange 324 extending radially from the cylindrical housing 320. Shaft 316 extends thought the cylindrical housing 320 and it rotatably supported therein by two longitudinally-spaced needle bearing braces 322, 323. A vortexing wheel, which in the illustrated embodiment comprises a vortexing pulley 326, is attached to the shaft 316 at an intermediate portion thereof, and the counterweight 180 is attached to the shaft 316 at its upper end.

Vortex drive motor 302 is preferably a stepper motor and may include a rotary encoder. The vortex transmission may include feedback sensors. In the illustrated embodiment, an index wheel 312 is attached to the vortex drive pulley 310, and a rotational position of the index wheel 312, e.g., a "home" position, may be detected by a sensor 314, which may comprise a slotted optical sensor. Other types of sensors may be used for indicating a home position. Such sensors may comprise proximity sensors, magnetic sensors, capacitive sensors, etc.

In the illustrated embodiment, as shown in FIGS. 4 and 5, each of the eccentric couplings 332, 342, 352 extends above a corresponding vortexing rotating element which, in the illustrated embodiment, comprises a respective idler pulley 330, 340, 350. The vortexing idler pulleys 330, 340, 350 are mounted on and rotate with the turntable drive pulley 208 about the rotational center of the drive pulley 208. The eccentric couplings 342, 352, 362, or portions thereof, extend through the turntable 150 as shown in FIG. 6, so as to rotationally couple the turntable 150 to the turntable drive pulley 208 such that rotation of the turntable drive pulley causes a corresponding rotation of the turntable 150.

The eccentric couplings 332, 342, 352 also comprise a portion of the vortex transmission 308. Some or all of the eccentric couplings 332, 342, 352 are coupled to the vortexing wheel to impart eccentric rotation to the coupled eccentric couplings. In the embodiment shown in FIGS. 4 and 5, the vortexing idler pulleys 330, 340, 350 are each rotatably mounted to the turntable drive pulley 208 and are coupled to the vortexing pulley 326. The axes of rotation of the idler pulleys 330, 340, 350 are each located at the same radial distance from the center of the vortexing pulley 326, which corresponds to the center of shaft 316, although is it not required that the axes be located at the same radial distance. Also, the vortexing idler pulleys 330, 340, 350 are positioned in an equiangular arrangement about the vortexing pulley 326 at 120° intervals, although it is not required that the vortexing pulleys be spaced at equal angular intervals.

Referring now to FIGS. 4 and 5, above the turntable drive pulley 208, a serpentine belt 328 extends around the vortexing pulley 326, the vortexing idler pulley 330, and the vortexing idler pulley 340. Rotation of the vortex drive pulley 310 by the vortex drive belt 306 and the vortex motor 302 causes rotation of the shaft 316 and thereby rotates the vortexing pulley 326. As can be appreciated from FIGS. 4 and 5, rotation of the vortexing pulley 326 causes corresponding rotation of the vortexing idler pulleys 330 and 340, via the serpentine belt 328.

Appropriate tension in the serpentine belt 328 is maintained by tension adjusters 380, 390 and 400. Tension adjuster 380 is located between the vortexing pulley 326 and vortexing idler pulley 330 and comprises a slide 382 disposed within a surface slot 220 formed in the turntable drive pulley 208, a tension wheel 386 rotatably mounted to the slide 382, and a tension adjuster screw 384 extending through the slide 382 and through a through slot 210 formed in the turntable drive pulley 208. The tension wheel 386 bears against the serpentine belt 328, and tension in the belt 328 is adjusted by loosening the tension adjuster screw 384 so as to permit the slide 382 to move within surface slot 220 relative to the serpentine belt 328. The tension adjuster screw 384 is then retightened to fix the slide 382 and the tension wheel 386 at a position that provides the desired tension in the serpentine belt 328.

Tension adjuster 390 is located between vortexing idler pulley 330 and vortexing idler pulley 340 and comprises a slide 392 disposed within a surface slot 220 formed in the turntable drive pulley 208, a tension wheel 396 rotatably mounted to the slide 392, and a tension adjuster screw 394 extending through the slide 392 and through a through slot 210 formed in the turntable drive pulley 208. The tension wheel 396 bears against the serpentine belt 328, and tension in the belt 328 is adjusted by loosening the tension adjuster screw 394 so as to permit the slide 392 to move within the surface slot 220 relative to the serpentine belt 328. The tension adjuster screw 394 is then retightened to fix the slide 392 and the tension wheel 396 at a position that provides the desired tension in the serpentine belt 328.

Similarly, tension adjuster 400 is located between the vortexing pulley 326 and the vortexing idler pulley 340 and comprises a slide 402 disposed within a surface slot 220 formed in the turntable drive pulley 208, a tension wheel 406 rotatably mounted to the slide 402, and a tension adjuster screw 404 extending through the slide 402 and through a through slot 210 formed in the turntable drive pulley 208. The tension wheel 406 bears against the serpentine belt 328, and tension in the belt 328 is adjusted by loosening the tension adjuster screw 404 so as to permit the slide 402 to move within the surface slot 220 relative to the serpentine belt 328. The tension adjuster screw 404 is then retightened to fix the slide 402 and tension wheel 406 at a position that provides the desired tension in the serpentine belt 328.

There are three tension adjusters 380, 390, 400—one for each span of the serpentine belt 328 between vortexing idler pulley 330 and vortexing idler pulley 340, between vortexing idler pulley 340 and vortexing pulley 326, and between vortexing pulley 326 and vortexing idler pulley 330—in order to adjust the phase of the eccentric couplings 332, 342, 352 relative to each other. The tension adjusters 380, 390, 400 on the serpentine belt 328 serve at least a couple purposes. First, the tension adjusters tension the belt 228. In addition, the tension adjusters 380, 390, 400 clock the eccentric couplings 332, 342, 352 in phase. The tension adjusters 380, 390, 400 also clock the counter weight 180 180 degrees out-of-phase with the eccentric couplings 332, 342, 352. In one embodiment, there are no adjustments of the eccentric couplings 332, 342, 352 relative to the pulley teeth on the vortexing idler pulleys 330, 340 and the vortexing pulley 326. Accordingly, the eccentric couplings 332, 342, 352 and the counterweight 180 can be clocked in-phase by adjusting the belt length between each of the three pulleys idler pulleys 330, 340, 350.

It is important that each of the eccentric couplings 332, 342, and 352 have the same amount of offset (i.e., eccentricity) with respect to the respective vortexing idler pulleys 330, 340, 350. Also, the rotational positions of the vortexing idler pulleys 330, 340, 350 must be coordinated so that each eccentric coupling 332, 342, 352 is at the same rotational position with respect to the axis of rotation of the corresponding vortexing idler pulley 330, 340, 350, or the vortex drive system 700 may bind. This can be accomplished by adjusting the belt length between the vortexing idler pulleys 330, 340, 350 using the tension adjusters 380, 390, 400 as described above.

As explained above, the eccentric couplings 332, 342, and 352 are coupled to the turntable 150. Each of the eccentric couplings 332, 342, and 352 is positioned at an eccentric, or offset, location with respect to the rotational center of the corresponding vortexing idler pulley 330, 340 and 350. Thus, rotation of the vortexing idler pulleys 330 and 340, via the serpentine belt 328 and the vortexing pulley 326, causes an oscillating, vortexing motion of each of the eccentric couplings 332 and 342 that is imparted to the turntable 150 coupled thereto. The vortexing idler pulley 350 in the illustrated embodiment is not coupled to the vortexing pulley 326 via the serpentine belt 328. The vortexing pulley 350, with eccentric coupling 352 extending therefrom, is a follower that provides a third point of support for the turntable 150 and moves in the same vortexing path with the turntable 150.

The vortex motion of the turntable 150, as caused by the vortex drive system 300, is illustrated in FIG. 13. As explained above, during the vortex motion, the turntable 150 is moved by the eccentric rotation of the eccentric couplings 332, 342, such that the center "C" of the turntable 150 orbits about a vortex circle $C_V$ centered at an orbital center $C_O$ through positions $C_1$, $C_2$, $C_3$, $C_4$ as the turntable moves through positions $150_1$, $150_2$, $150_3$, $150_4$. During the vortex motion, every point of the turntable 150 orbits around a circle having the same radius as $C_V$. The radius of $C_V$ corresponds to the amount of eccentric offset of the eccentric couplings 332, 342, 352 with respect to the axes of rotation of the vortexing idler pulleys 330, 340, 350.

The purpose of the counterweight 180 is to minimize the vibration generated by the apparatus so as to limit the vibration that will be imparted by the apparatus to an instrument or laboratory in which the apparatus is employed. The counterweight 180 is attached to shaft 316 and is located beneath the container tray 110. The rotation pattern of the turntable 150 and container tray 110 relative to the motion of the counterweight 180 is similar to that of a camshaft. In one embodiment, the mass×radius product of the counterweight 180 is equal to: (the mass of the container support platform, i.e., the mass of the turntable 150 and the container tray 110)×(its effective radius)+(½ the mass of a full set of bottles occupying each container receptacle 112, 116 in the container tray 110, e.g., fourteen bottles in container tray 110 shown in FIG. 1)×(the effective radius of the bottles).

Of course the mass of the counterweight 180 can vary, which will have an effect on the resulting vibration of the apparatus depending on the liquid level of the bottles on the container tray 110. Selecting a counterweight mass equal to half the expected mass of a complete collection of full bottles provides a reasonable middle ground. Any vibration in the apparatus is due to the varying fluid levels in the bottles to the extent the levels are above or below the ideal/calibrated mass of the counterweight. So, as a percentage of the overall mass of the apparatus, the potential variability of the mass of the fluid in the bottles is low, which provides for minimal vibrations.

Also, one could increase the mass of the turntable and container tray (and the counterweight) to reduce the overall effect of the mass variability caused by the changing liquid levels in the bottles, but that would require larger turntable drive and vortex drive motors.

There are a number of benefits to providing the counterweight 180. First, the reduced vibrations achieved with the use of a counterweight improves operational lifetime of the apparatus, and particularly the drive motors, since the drive systems will be subject to decreased vibration levels. Furthermore, the apparatus may be employed in a diagnostic instrument that requires very precise movements and fluid dispensing with very small spatial tolerances for accurate operation of its many moving parts, such as a fluid dispensing pipettor. The introduction of excessive vibrations into such a calibrated environment could negatively impact the accurate positioning of the pipettor and/or other modules. Such inaccuracies could result in, for example, system failures, contamination, sample processing failures, and related issues.

Figure 7:
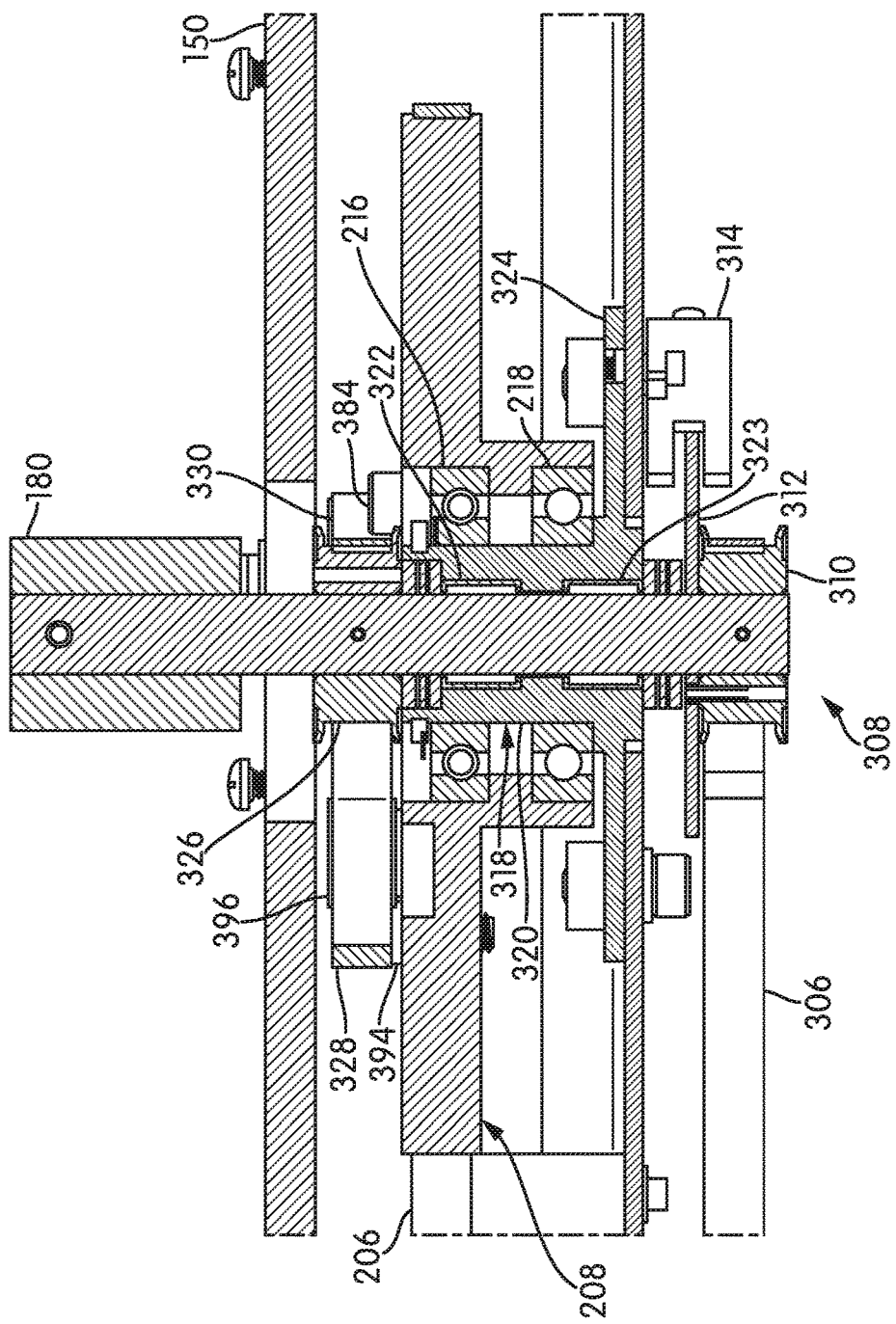
FIG. 7 is a partial cross-sectional view of the apparatus along the line VII-VII in FIG. 5.

Details of the rotational mounting of the turntable drive pulley 208 and the vortexing pulley 326 are shown in FIG. 7, which is a partial transverse cross-section of the apparatus along the line VII-VII in FIG. 5. As shown in FIG. 7, the turntable drive pulley 208 is rotationally supported with respect to the non-rotating cylindrical housing 320 of the shaft bearing 318 by means of upper and lower bearing races 216, 218. The shaft 316 is rotationally supported within the shaft bearing 318 by the spaced-apart needle bearing races 322, 323 located within the fixed, non-rotating cylindrical housing 320 of the shaft bearing 318. Bearing races 216, 218 rotationally isolate the turntable drive pulley 208 from the vortex transmission 308. Accordingly, the turntable drive pulley 208 is able to rotate independently of the shaft 316 and the vortex drive pulley 310 and vortexing pulley 326 connected thereto. Moreover, the vortex transmission 308, comprising the shaft 316, the vortex drive pulley 310 and the vortexing pulley 326, can rotate independently of the turntable drive system 200, comprising the turntable drive motor 202, the turntable drive belt 206, and the turntable drive pulley 208. Thus, the container tray 110 can be selectively rotated by the turntable drive system 200 to place any of the containers carried thereon into a desired rotational position, or the entire container tray 110 can be moved in a vortexing motion by the vortex drive system 300 to agitate the contents of the containers carried thereon. The rotating motion and the vortexing motion can be performed independently. In certain particularly preferred embodiments, the rotating motion and vortexing motion are performed independently.

Figure 8:
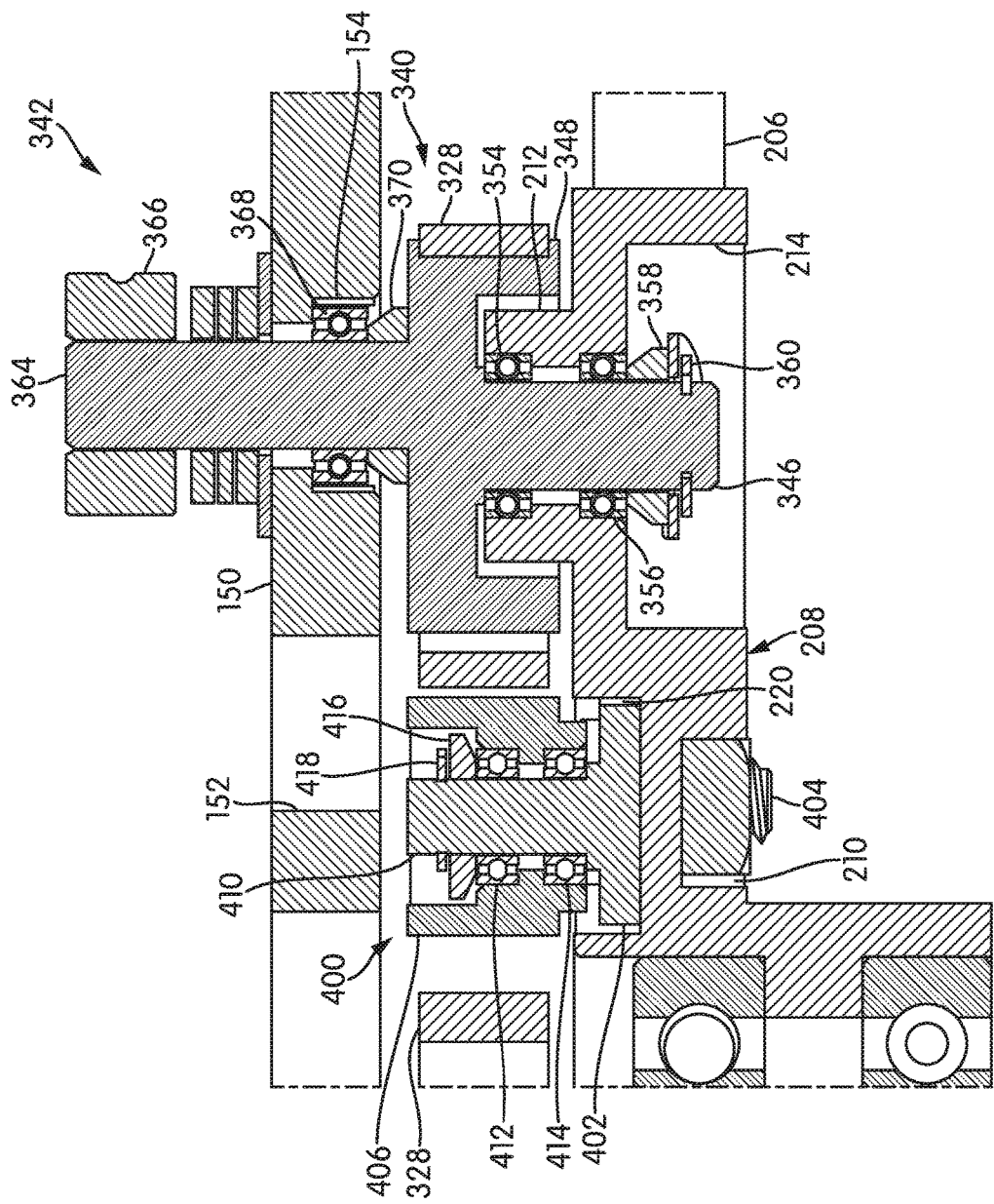
FIG. 8 is a partial cross-sectional view of the apparatus along the line VIII-VIII in FIG. 5.

Details of the vortexing idler pulley 340 and details of the tension adjuster 400 are shown in FIG. 8, which is a partial cross-section of the apparatus 100 along the line VIII-VIII in FIG. 5. The vortexing idler pulley 340 comprises a pulley wheel 348 and a central idler pulley shaft 346 extending downwardly from the pulley wheel 348. The pulley wheel 348 is hollowed out on its underside and nests upon a raised cylindrical boss 212 of the turntable drive pulley 208. The idler pulley shaft 346 extends through a central axial opening formed through the raised boss 212 and is rotationally supported at spaced apart bearing races 354 and 356. The end of the idler pulley shaft 346 terminates within a cylindrical recess 214 formed in the underside of the turntable drive pulley 208. A frustoconical shim washer 358 disposed on a lower end of the idler pulley shaft 346 bears against the inner race of the lower race bearing 356, and a snap retainer clip 360 on the end of the shaft 346 secures the idler pulley 340 in place. The end of the idler shaft pulley 346, the shim washer 358, and the snap retainer clip 360 are all disposed within the recess 214 so that no portions of the vortexing idler pulley 340 extends below the bottom of the turntable drive pulley 208.

The eccentric coupling 342 comprises an eccentric shaft 364 extending upwardly from the pulley wheel 348 at an offset position with respect to the idler pulley shaft 346. The eccentric shaft 364 extends through an opening in the turntable 150 and is rotationally supported by a bearing race 368 disposed within a recess 154 formed in the underside of the turntable 150 with a frustoconical shim washer 370 disposed between the top of the pulley wheel 348 and the bottom of the bearing race 368. A cap 366 is rotatably mounted on an upper end of the eccentric shaft 364 extending above the turntable 150 so as to be rotatable with respect to the shaft 364.

The vortexing idler pulleys 330 and 350 each comprise an assembly that is substantially identical to that of vortexing idler pulley 340 shown in FIG. 8.

The tension adjuster 400 includes a wheel shaft 410 extending upwardly from the slide 402. The tension wheel 406 is coaxially mounted on the wheel shaft 410 and is rotatably supported with respect to the wheel shaft 410 by upper and lower bearing races 412, 414 secured in place by a frustoconical shim washer 416 and a snap retainer clip 418 that are disposed within an upper recess of the tension wheel 406. The tension adjusting screw 404 extends through the slot 210 formed through the turntable drive pulley 208. The slide 402 is disposed within the surface slot 220 formed in the upper surface of the turntable drive pulley 208. Slot 152 formed in the turntable 150 provides access to the tension adjuster 400. The orbital path of the turntable 150 with respect to the turntable drive pulley 208 due to the eccentric rotation of the eccentric couplings 332, 342, 352 causes the positions of the slots 152 to move with respect to the tension adjusters 380, 390, 400. Thus, the turntable 150 can be moved with respect to the turntable drive pulley 208 to align the slots with the eccentric couplings 332, 342, 352.

Tension adjusters 380 and 390 comprise an assembly that is substantially identical to that of tension adjuster 400 shown in FIG. 8.

Figure 9:
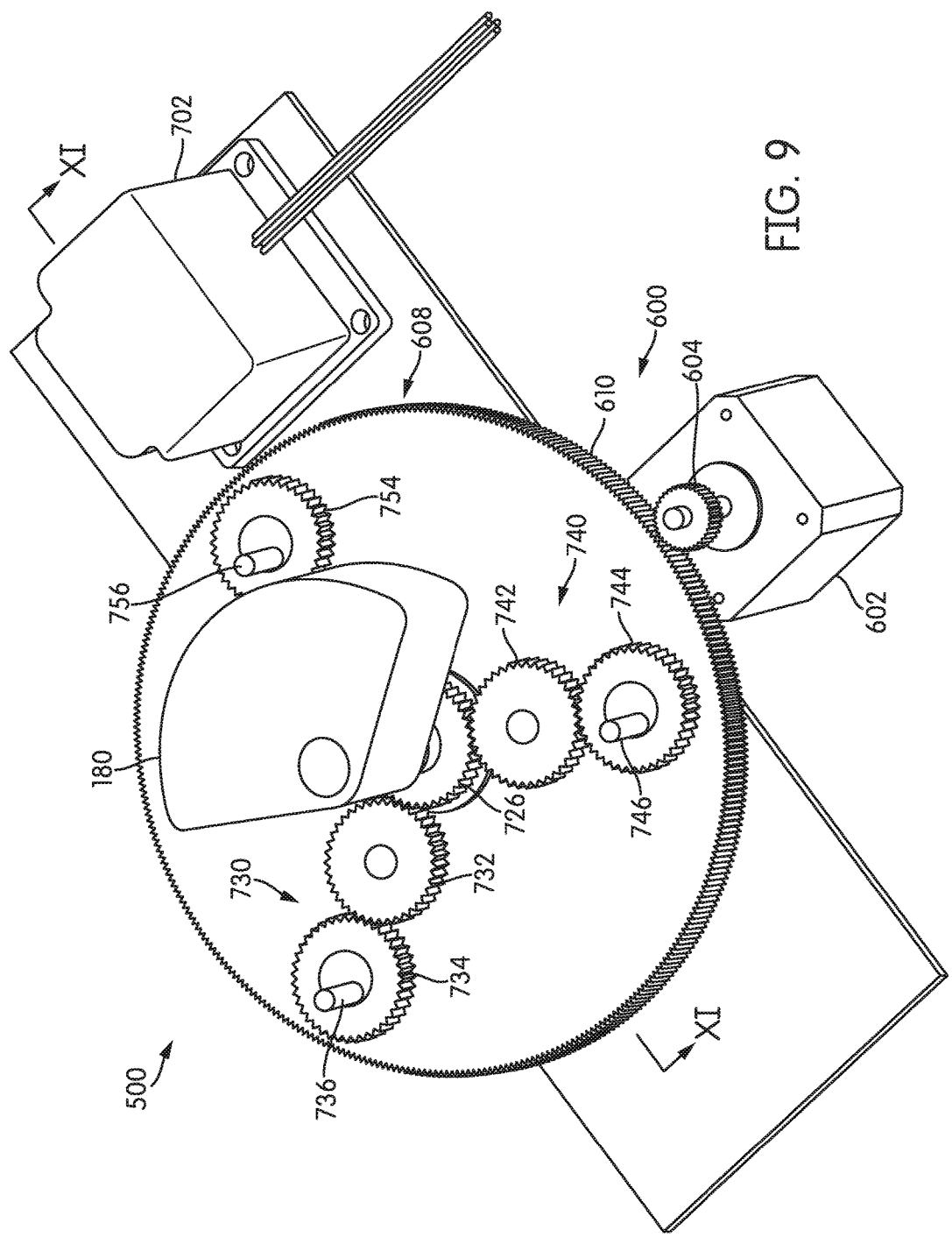
FIG. 9 is a top perspective view of an alternate embodiment of a fluid container mixing apparatus embodying aspects of the disclosure shown without a container tray or a turntable.
Figure 10:
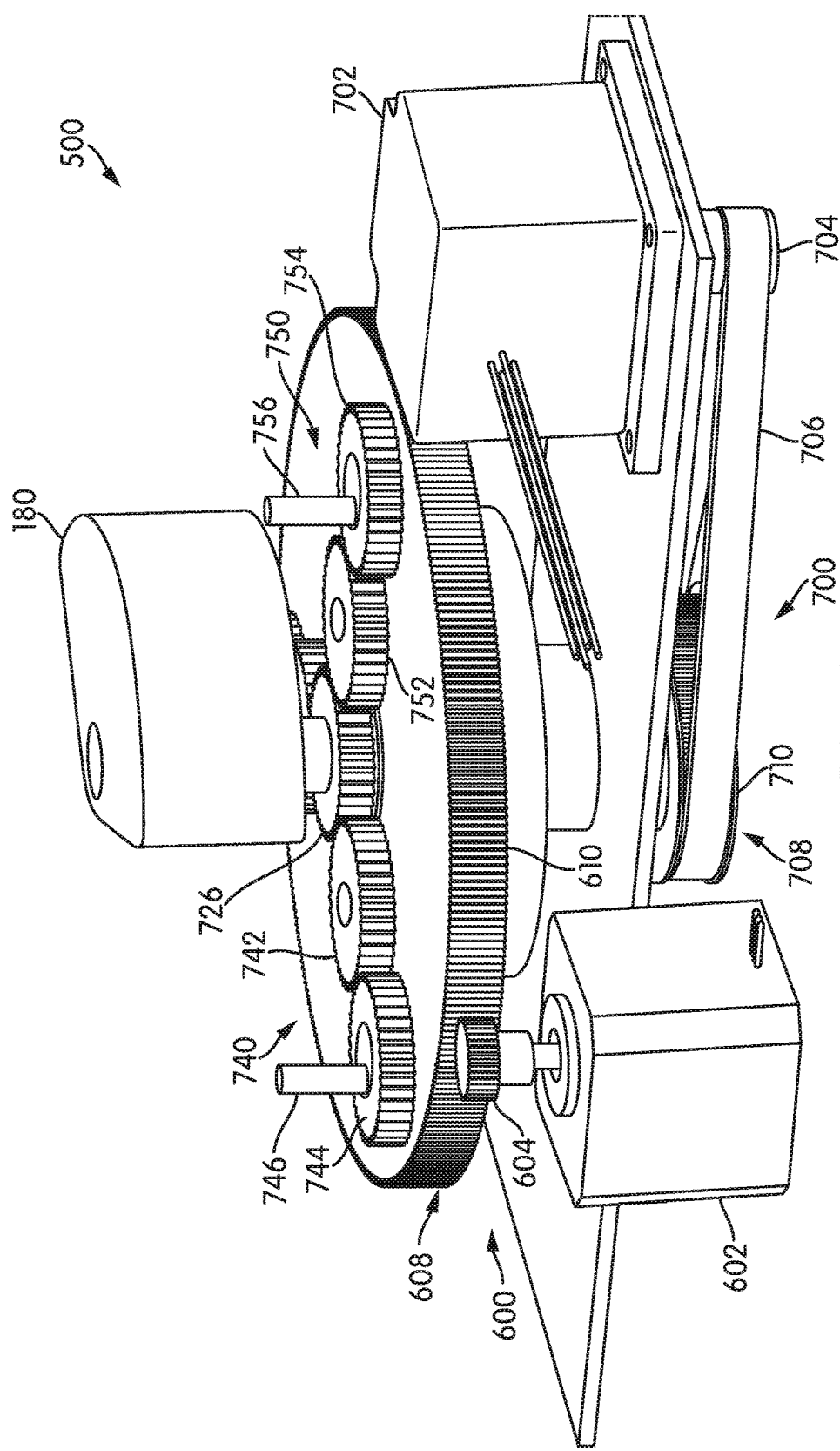
FIG. 10 is a top perspective view of the apparatus shown in FIG. 9.
Figure 11:
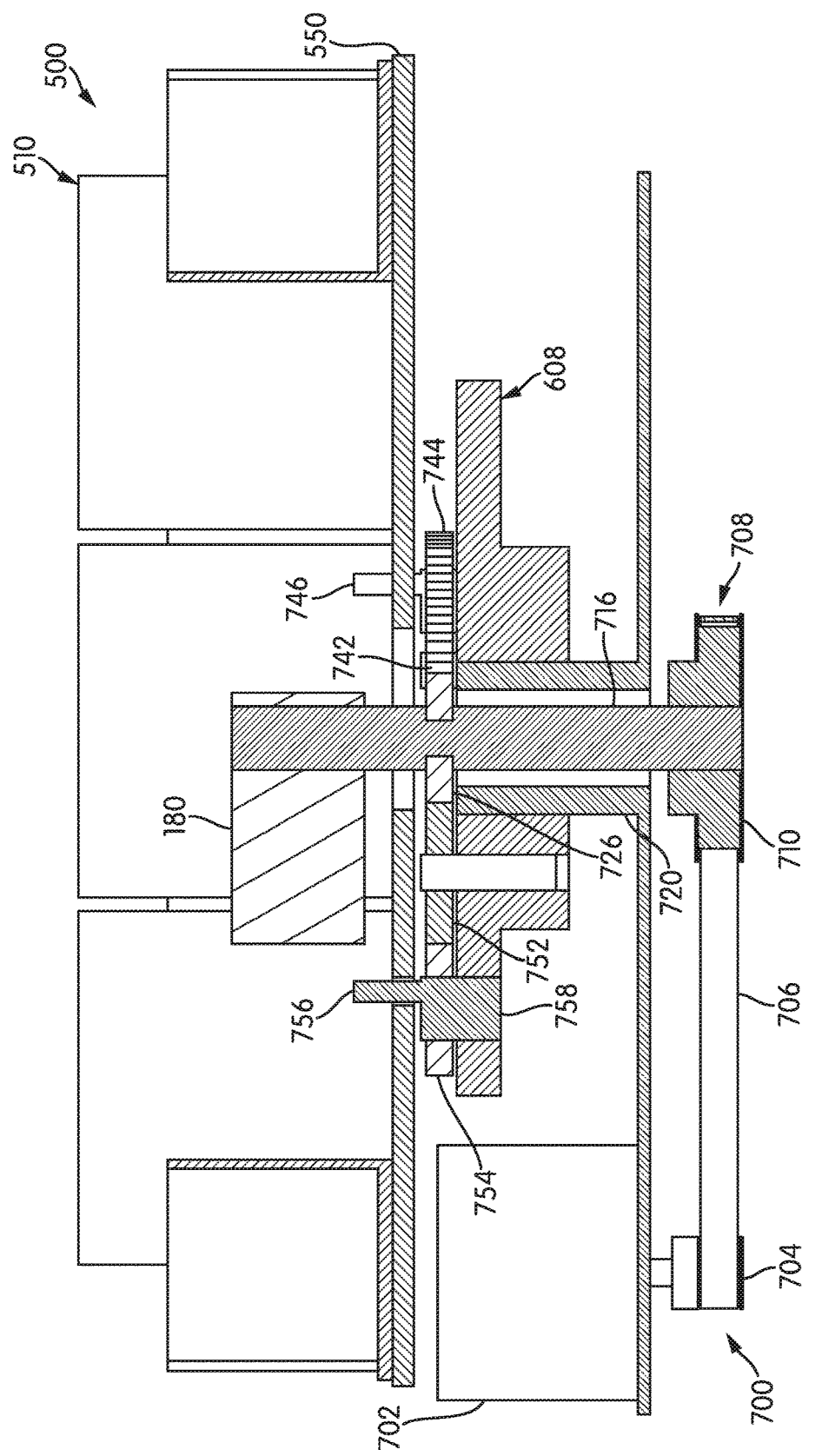
FIG. 11 is a cross sectional view of the apparatus along the line XI-XI in FIG. 9 and showing a turntable and container tray.

An alternate embodiment of a fluid mixing apparatus embodying aspects of the present disclosure is indicated by reference number 500 in FIGS. 9, 10 and 11. The apparatus 500 includes a container support platform configured to hold one or more fluid container and to be indexed to selectively present fluid containers to a defined position. In the illustrated embodiment, the container support platform is configured to be rotatable about an axis of rotation. The container support platform is also configured to be movable in a vortexing, or orbital path about an orbital center.

In the illustrated embodiment, the container support platform comprises a fluid container tray 510 and a turntable 550 (FIG. 11).

Apparatus 500 includes a turntable drive system 600 coupled to the container support platform and constructed and arranged to effect powered rotation of the fluid container support platform about its axis of rotation. Apparatus 500 further includes a vortex drive system 700 coupled to the fluid container support platform and configured to effect vortexing, orbital movement of the fluid container support platform about an orbital center. FIGS. 9 and 10 are top perspective views of the turntable drive system 600 and the vortex drive system 700 of the apparatus shown without the turntable or fluid container tray. FIG. 11 is a cross section along the line XI-XI of FIG. 9 and shows the vortex drive system 700, the turntable 550, and the container tray 510.

Referring to FIGS. 9 and 10, the turntable drive system 600 includes a turntable drive motor 602, preferably a stepper motor, having a driveshaft gear 604 attached to an output shaft of the motor. The turntable drive motor 602 is coupled to the fluid container support platform by the engagement of the driveshaft gear 604 with the peripheral gear teeth of a turntable drive gear 608. Rotation of the driveshaft gear 604 by the turntable drive motor 602 causes a corresponding rotation of the turntable drive gear 608 about its axis of rotation.

Referring to FIG. 10, the vortex drive system 700 includes a vortex drive motor 702 having a driveshaft wheel 704 coupled to a vortex drive pulley 710 of a vortex transmission 708 by means of a vortex drive belt 706 (or gears or other known means for coupling the vortex drive motor 702). Referring to FIG. 11, the vortex transmission 708 of apparatus 500 further includes a vortexing wheel, which, in the illustrated embodiment, comprise vortexing gear 726 disposed above the turntable drive gear 608 and connected by a shaft 716 to the vortex drive pulley 710. A counterweight 180 is attached to an upper, free end of the shaft 716. The shaft 716 is rotationally supported within a fixed bearing housing 720, for example, using one or more bearing races or other forms of bearings (not shown). The turntable drive gear 608 is rotationally supported on the outside of the bearing housing 720, also by suitable bearings, bearing races, or other suitable means (not shown), so that the turntable drive gear 608 and the vortex drive pulley 710 and shaft 716 can rotate independently of each other.

The vortex transmission 708 further includes eccentric vortex couplings 736, 746, 756. As shown in FIGS. 9 and 10, each of the eccentric couplings 736, 746, 756 extends above a rotating vortexing element which, in the illustrated embodiment, comprises a respective end gear 734, 744, 754. Each eccentric vortex coupling 736, 746, 756 is coupled to the vortexing gear 726 by a gear train. Specifically, the eccentric vortex coupling 736 is rotated by a gear train 730 comprising a transfer gear 732 directly engaged with the vortexing gear 726 and end gear 734 that is directly engaged with the transfer gear 732. The eccentric vortexing coupling 736 extends axially from the end gear 734 and is eccentrically offset with respect to the axis of rotation of the end gear 734.

The eccentric vortex coupling 746 is rotated by a gear train 740 comprising a transfer gear 742 directly engaged with the vortexing gear 726 and end gear 744 that is directly engaged with the transfer gear 742. The eccentric vortexing coupling 746 extends axially from the end gear 744 and is eccentrically offset with respect to the axis of rotation of the end gear 744.

The eccentric vortex coupling 756 is rotated by a gear train 750 comprising a transfer gear 752 directly engaged with the vortexing gear 726 and end gear 754 that is directly engaged with the transfer gear 752. The eccentric vortexing coupling 756 extends axially from the end gear 754 and is eccentrically offset with respect to the axis of rotation of the end gear 754.

The end gears 734, 744, 754 are each rotatably mounted to the turntable drive gear 608. The axes of rotation of the end gears 734, 744, 754 are each located at the same radial distance from the center of the vortexing gear 726, which corresponds to the center of shaft 716, although it is not required that the gears be located at the same radial distance. Also, the end gears 734, 744, 754 are positioned in an equiangular arrangement about the vortexing gear 726 at 120° intervals, although it is not required that he end gears be positioned at equal angular intervals.

In alternate embodiments, the gear trains may comprise more than two gears, so long as there is an even number of gears (e.g., 2, 4, 6, etc.), in the gear train so that the vortexing gear 726 rotates in the same direction as the end gears 734, 744, 754 in order to properly counterbalance the mechanism.

Rotation of each of the end gears 734, 744, 754 causes corresponding vortexing, orbital movement of the corresponding eccentric couplings 736, 746, 756 that is imparted to the container tray 510. Thus, via the gear trains 730, 740, 750, rotation of the vortexing gear 726 causes corresponding rotations of the eccentric vortex couplings 736, 746 756 that imparts the vortexing orbital movement to the container tray 510.

As shown in FIG. 11, eccentric vortex coupling 756 extends from shaft 758 rotationally mounted within the turntable drive gear 608 and having a central axis of rotation that defines the central axis of the end gear 754. Shaft 758 may be supported with respect to a through hole formed through the turntable drive gear 608 by means of bearings (not shown). The coupling 756 is offset from the axis of rotation of the shaft 758. Each of the eccentric vortex couplings 736 and 746 has a construction that is similar to that of eccentric vortex coupling 756.

The eccentric vortex couplings 736, 746, 756 extend through the turntable 550 and thereby rotationally couple the turntable 550 with the turntable drive gear 608 so that rotation of the turntable drive gear about its axis of rotation causes a corresponding rotation of the turntable 550 and the fluid container tray 510 attached thereto.

Figure 12:
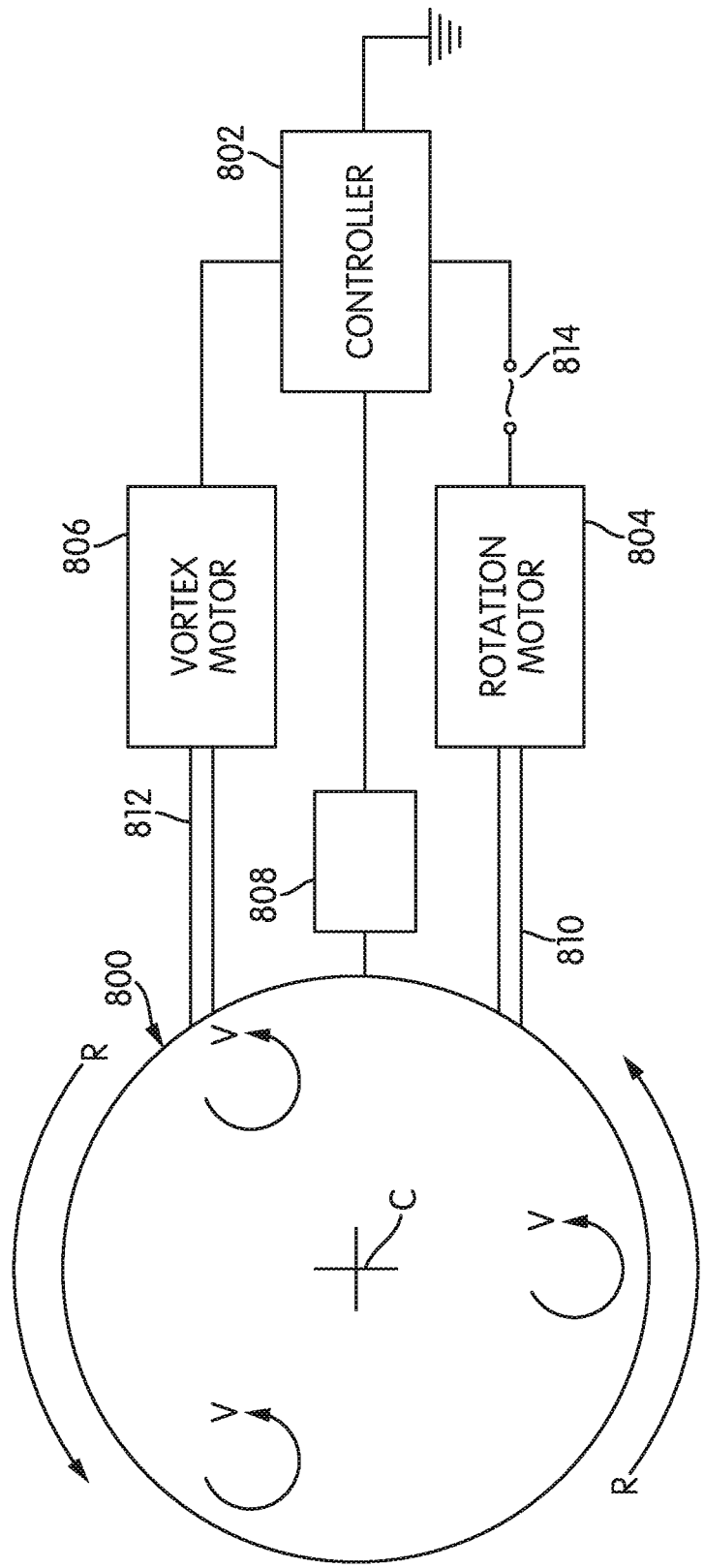
FIG. 12 is a schematic view of a power and control system of the fluid container mixing apparatus.

FIG. 12 is a schematic view of the control system for controlling operation of the fluid container mixing apparatus embodying aspects of the present disclosure. A fluid container mixing apparatus configured to provide independent positioning, e.g., by rotation of the apparatus, of one or more containers carried on the apparatus and vortexing of the containers to agitate the contents of the containers is indicated by reference number 800 in FIG. 12. Apparatus 800 may correspond to apparatus 100 or apparatus 500 described above. The positioning motion of the apparatus is represented by the arrows "R", which represents rotation of the apparatus about the center C. Vortexing of the apparatus is represented by the three arrows "V". The rotation of the apparatus is effected by an indexing drive system comprising an indexing motor 804 that is coupled to the apparatus 800, as represented by double lines 810, to effect powered rotation of the apparatus. Vortex motion V of the apparatus is effected by a vortex drive system comprising a vortex motor 806 that is coupled to the apparatus 800, as represented by double lines 812, to effect powered vortexing motion of the apparatus. The indexing motor 804 and the vortex motor 806 are coupled to and controlled by a controller 802 that is also connected to a controllable power supply 814. Controller 802 provides power and operational control signals to the indexing motor 804 and vortex motor 806. Controller 802 may also receive data from the indexing motor 804 and the vortex motor 806 in the form of rotary encoder counts as well as other feedback sensor signals. Box 808 represents feedback sensors coupled to the mixing apparatus 800, such as a rotational home flag, a vortex position home flag, etc., and is connected to the controller 802 for providing positional, or other status, feedback that is used in generating control signals for operating the indexing motor 804 and the vortex motor 806.

Evaporation-Limiting Container Insert

The fluid contents of containers carried on the fluid container support platform of the mixing device 100 or 500 may comprise fluid solutions or suspensions. Representative fluid contents may comprise reagents containing solid supports, such as silica or magnetically-responsive particles or beads. See, e.g., Boom et al., U.S. Pat. No. 5,234,809 and Weisburg et al., U.S. Pat. No. 6,534,273. Such solid supports can be useful for immobilizing nucleic acids in a sample processing procedure to remove inhibitors of amplification and/or detection. Suitable reagents for this purpose include the target capture reagents described above. As discussed elsewhere in this disclosure, mixing of the fluid contents, e.g., by agitating the container containing the fluid contents, helps to maintain the suspended materials in suspension within the fluid.

Even in the absence of suspended particles or solid supports, it may be possible for one or more components of a fluid solution to precipitate out of solution, potentially affecting the concentration of the solution that is drawn out of the container. Even small changes in concentrations can have a deleterious impact on a test or assay performed with such solutions. Mixing the fluid contents, e.g., by agitating the container containing the fluid contents, may actually slow and/or reverse such precipitation.

The containers are typically carried in an open state to permit ready access to the fluid contents of each of the containers by a fluid transfer apparatus, such as a robotic pipettor. The fluid transfer apparatus may access the fluid contents of the container to withdraw fluid from the container and/or to dispense additional fluid into the container.

The fluid transfer apparatus may include a pipettor configured to detect a fluid surface within the container, e.g., for the purpose of determining or verifying the height of the fluid within the container, which can be used to calculate the volume of fluid remaining in the container. Suitable pipettors for this purpose are disclosed by Lipscomb et al. in U.S. Pat. No. 6,914,555.

When the containers are in an open state, the fluid contents of the containers are exposed to the atmosphere and, therefore, are susceptible to evaporation. Mixing only exacerbates this problem, as mixing results in increased exposure of a fluid surface to the atmosphere, thereby potentially accelerating the rate of evaporation.

Figure 15:
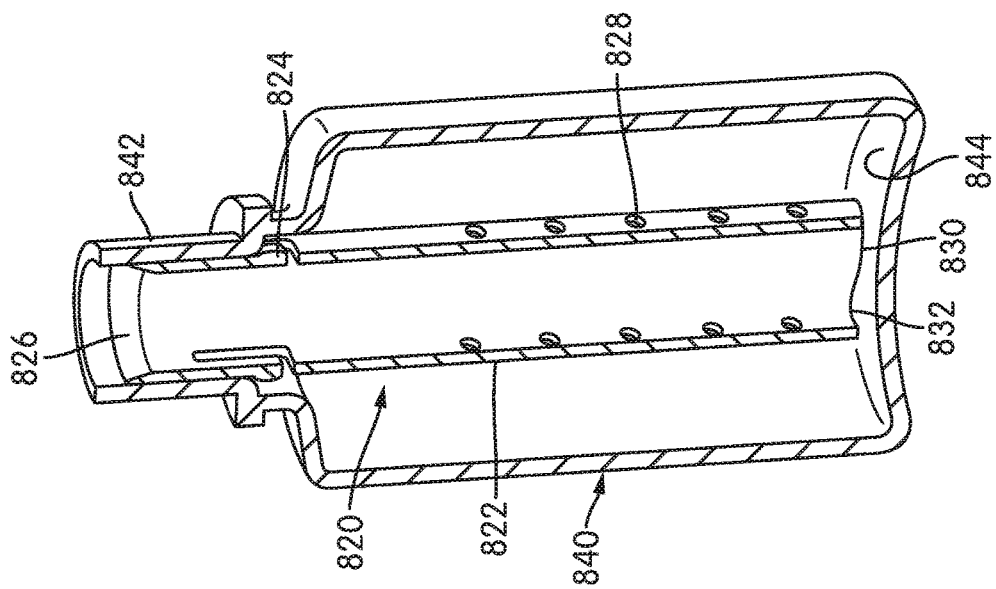
FIG. 15 is a cross-sectional, perspective view of the container insert inserted into a container.
Figure 14:
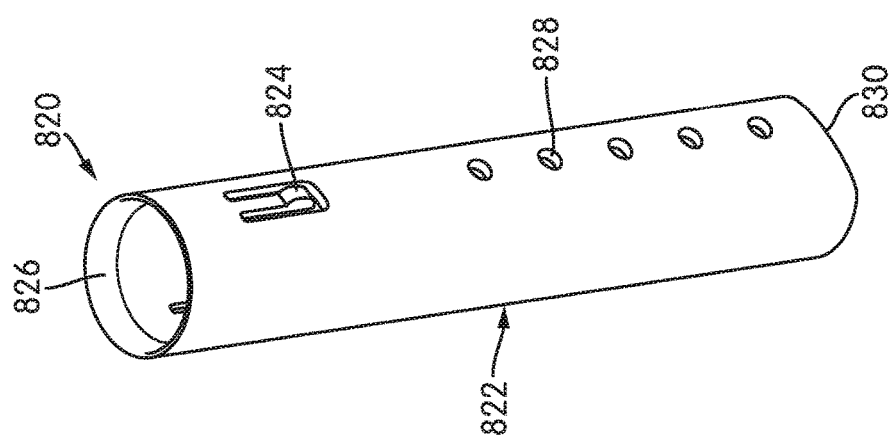
FIG. 14 is a perspective view of an evaporation-limiting container insert.

An evaporation-limiting container insert for reducing the amount of evaporation from a container is indicated by reference number 820 in FIGS. 14 and 15. The insert 820 includes an elongated tubular body 822 with a plurality of holes 828 formed in a side wall of the tubular body 822. In an exemplary embodiment, the tubular body 822 is cylindrical and has a generally constant diameter from one end thereof to an opposite end thereof. The holes 828 may be circular, as shown, or may have another shape. The shape of the holes 828 may be dictated by practicalities of manufacturing. In one embodiment, the size of each hole 828 is about $\frac{1}{16}$ inch, but may be of any suitable size. When the fluid contents of the container include a suspension of solid or semi-solid particles, the holes 828 should be sized to permit the passage of the particles through the tubular body 822 of the container insert 820.

In an embodiment, the holes 828 may be longitudinally aligned along the tubular body 822 and may be provided on one or more sides of the tubular body 822. There is no requirement that the holes 828 be aligned, as shown in the figures. The arrangement of the holes may be dictated by considerations, such as manufacturing practicalities. The holes 828 may be provided in two or more groups—e.g., lines—of holes located at diametrically opposed locations on the body 822 or otherwise spaced around the body 822. In various embodiments, there are at least three holes 828 on each of two opposed sides of the container insert 820, and there may be 4, 5, 6 or more holes 828 on each of two opposed sides of the insert 820 in such embodiments.

In various embodiments, the insert 820 may include a beveled surface 826 surrounding a top opening and an irregular or undulating bottom edge 830.

FIG. 15 is a cross-sectional, perspective view of the container insert 820 inserted into a representative container 840. In this embodiment, the insert 820 is inserted into the container 840 through an opening at the top of a neck 842 of the container 840. In an exemplary embodiment, the outside dimension of the tubular body 822 (e.g., the outside diameter) conforms to, i.e., is only slightly smaller than, the inside dimension (e.g., diameter) of the neck 842 so that the container insert 820 snugly fits within the container 840. In various embodiments, an insert retainer feature, such as a detent 824, resiliently engages the inside surface of the neck 842 to help retain the insert within the container 840. The beveled surface 826 surrounding the top opening of the insert 820 will help to redirect a misaligned a fluid transfer apparatus (e.g., pipettor tip component) toward the center of the insert 820.

As shown in FIG. 15, the length of the container insert 820 may be such that a top end of the insert 820 is disposed at or just below the top of the container neck 842 and the lower end 830 of the insert 820 is in contact with the bottom 844 of the container 840. While not a requirement, having the container insert 820 in contact with the bottom 844 of the container 840 can aid in stabilizing the insert within the container 840. This may be important when accessing the container 840 with a pipette tip, especially a pipette tip capable of facilitating level sensing (e.g., capacitive level sensing) and a system configured to initiate fluid aspiration at the pipette tip upon detected contact of the pipette tip with a fluid surface, as contact between the pipette tip and a misaligned insert could cause a pipettor of an associated analyzer to prematurely initiate an aspiration step. The irregular or undulating bottom edge 830 of the container insert 820 prevents the bottom edge 830 from forming a sealing contact with the bottom 844 of the container 840. The shape of the bottom edge 830 also creates one or more gaps 832 between the bottom edge 830 of the container insert 820 and the bottom 844 of the container 840 that promote filling and removal of the fluid contents of the container 840.

The benefit of the insert 820 is that it limits the amount of a fluid surface within the container 840 that is exposed to the atmosphere and, thus, reduces the amount of fluid evaporation when compared to the container 840 without the insert 820. This is because only the fluid surface within the tubular body 822 is exposed to atmosphere. As a result, loss of fluid to evaporation loss is minimized, thereby making more of the fluid available for the intended use. Reducing evaporation also increases the stability of the open container 840 on the instrument.

While the container insert 820 is effective at retarding evaporation of a liquid from the container 840, its presence can interfere with mixing of the fluid contents within the container 840. This is because fluid contents within the container insert 820 can become isolated from fluid contents outside the container insert 820. The holes 828 formed in the tubular body 822 of the container insert 820, however, are configured to facilitate uniform mixing of fluid contents within the container insert 820 by allowing fluid within the container 840 to flow between the space inside the tubular body 822 and the space outside the tubular body 822. Moreover, the one or more recesses 832 between the bottom edge 830 of the container insert 820 and the bottom 844 of the container 840 allows fluid within the container 840 to mix and to enter the insert 820 through the recesses 832.

Accordingly, the holes 828 and the recesses 832 help promote the mixing of the fluid contents of the container 840—either a fluid suspension or a fluid solution—by allowing migration of fluid between the space inside the tubular body 822 and the area outside the tubular body 822, thus facilitating an exchange of relatively un-mixed fluid contents inside the tubular body 822 and relatively mixed fluid contents outside the tubular body 822. Proper mixing allows the particles of beads of a fluid suspension to remain uniformly dispersed within the fluid contents of the container 840.

It is noted that while holes formed in a container insert help to promote mixing of fluid contents within the insert, the use of such holes runs contrary to the purpose of the insert, which is to limit evaporation. As the fluid contents within a container fall below hole or set of holes, the fluid surface outside of the container insert becomes exposed to the atmosphere through the hole(s), and there is likely to be at least some evaporation through the exposed hole(s). Thus, the inventor discovered that an effective design of the container insert requires a balancing of the somewhat contradictory requirements of limiting fluid surface-atmosphere exposure on the one hand, and promoting adequate mixing of the fluid within the insert by enabling fluid movement into and out of the insert on the other hand.

In various embodiments, a majority of the holes 828 are located on a lower portion of the tubular body 822, meaning that all or most of the holes 828 are located below a midpoint of the length of the body 822, as shown in FIG. 14. While concentrating the holes 828 toward a lower end of the tubular body 822 may help reduce evaporation by delaying the time at which the fluid level falls below the top hole(s) 828 and the fluid surface outside of the container insert 820 becomes exposed to the atmosphere, extending the holes 828 toward the top of the body 822 may help promote better mixing, allowing for more fluid movement into and out of the insert 820.

Thus, the size, number, and positions of the holes, while ideally selected to limit evaporation, must be balanced with the need to provide adequate mixing. Mixing effectiveness may be empirically evaluated by, for example, taking optical density measurements with aliquots of the fluid contents taken from within and outside of a container insert following agitation of a container. The optical density measurements of these aliquots will be similar if the solid supports are uniformly distributed within the fluid contents.

Figure 16:
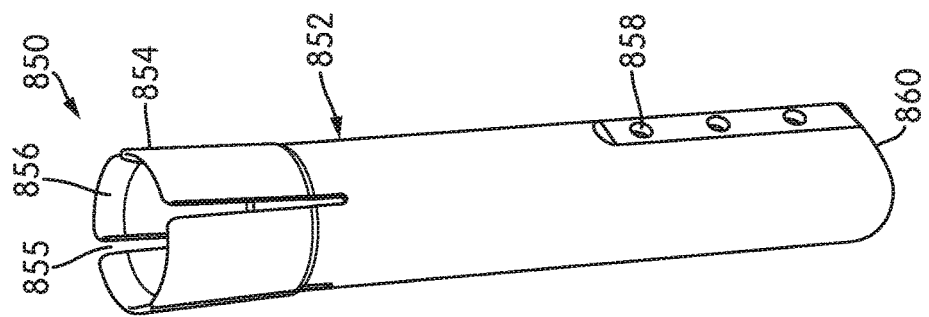
FIG. 16 is a perspective view of an evaporation-limiting container insert according to an alternate embodiment.

An alternate embodiment of a container insert for reducing the amount of evaporation from a container is indicated by reference number 850 in FIG. 16. The container insert 850 includes a tubular body 852 of generally constant width with a plurality of holes 858 formed in a side wall of the tubular body 852. In an exemplary embodiment, the tubular body 852 is cylindrical and has a generally constant diameter from one end thereof to an opposite end thereof. In an embodiment, the holes 858 may be longitudinally aligned along the tubular body 852 and may be provided on one or more sides of the tubular body 852. In various embodiments, a majority of the holes 858 are located on a lower portion of the tubular body 852, meaning that all or most of the holes 858 are located below a midpoint of the length of the tubular body 852. In another embodiment, the holes 858 are distributed throughout the length of the body 852. In various embodiments, there are at least three holes 858 on each of two opposed sides of the container insert 850, and there may be 4, 5, 6 or more holes 858 on each of two opposed sides of the insert 850 in such embodiments. In some embodiments, the container insert 850 includes a beveled surface 856 surrounding a top opening and an irregular or undulating bottom edge 860.

In various embodiments, an insert retainer feature of the container insert 850 includes a number of resilient tabs 854 (e.g., two or more) defined by angularly-spaced, axial slits 855 extending from a top edge of the insert 850. The tabs 854 are splayed radially outwardly so that the outer dimension (e.g., diameter) of the tubular body 852 in the vicinity of the tabs 854 is larger than the outer dimension of the remainder of the tubular body 852. The outer dimension of the lower end of the tubular body 852 is preferably smaller than the inside dimension of the container opening, so that the insert 850 is easily inserted into the opening. The outer dimension of the tubular body 852 in the vicinity of the tabs 854, however, is larger than the inside dimension of the container opening. The tabs 854 thus flex radially inwardly as the container insert 850 is fully inserted into the container opening, and the resilience of the tabs 854 creates a radial force between the tabs 854 and the inside of the container opening, thereby securing the insert 850 within the container.

In various embodiments, when the container insert 850 is fully inserted into a container, the lower end of each slit 855 separating a pair of tabs 854 extends below the neck of the container, thereby creating a small vent near the neck of the container to prevent a vacuum from forming in the container. This feature is illustrated with the container insert 870 of FIG. 17.

As with container insert 820 described above and shown in FIGS. 14 and 15, the holes 858 formed in the tubular body 852 of the insert 850 allow fluid within the container—including particles or beads in suspension—to flow between the space inside the tubular body 852 and the space outside the tubular body 852. Moreover, the undulating bottom edge 860 of the container insert 850 creates one or more recesses between the bottom edge 860 of the insert 850 and the bottom of the container which allows fluid within the container to mix and to enter the insert 850 through the recesses.

Figure 17:
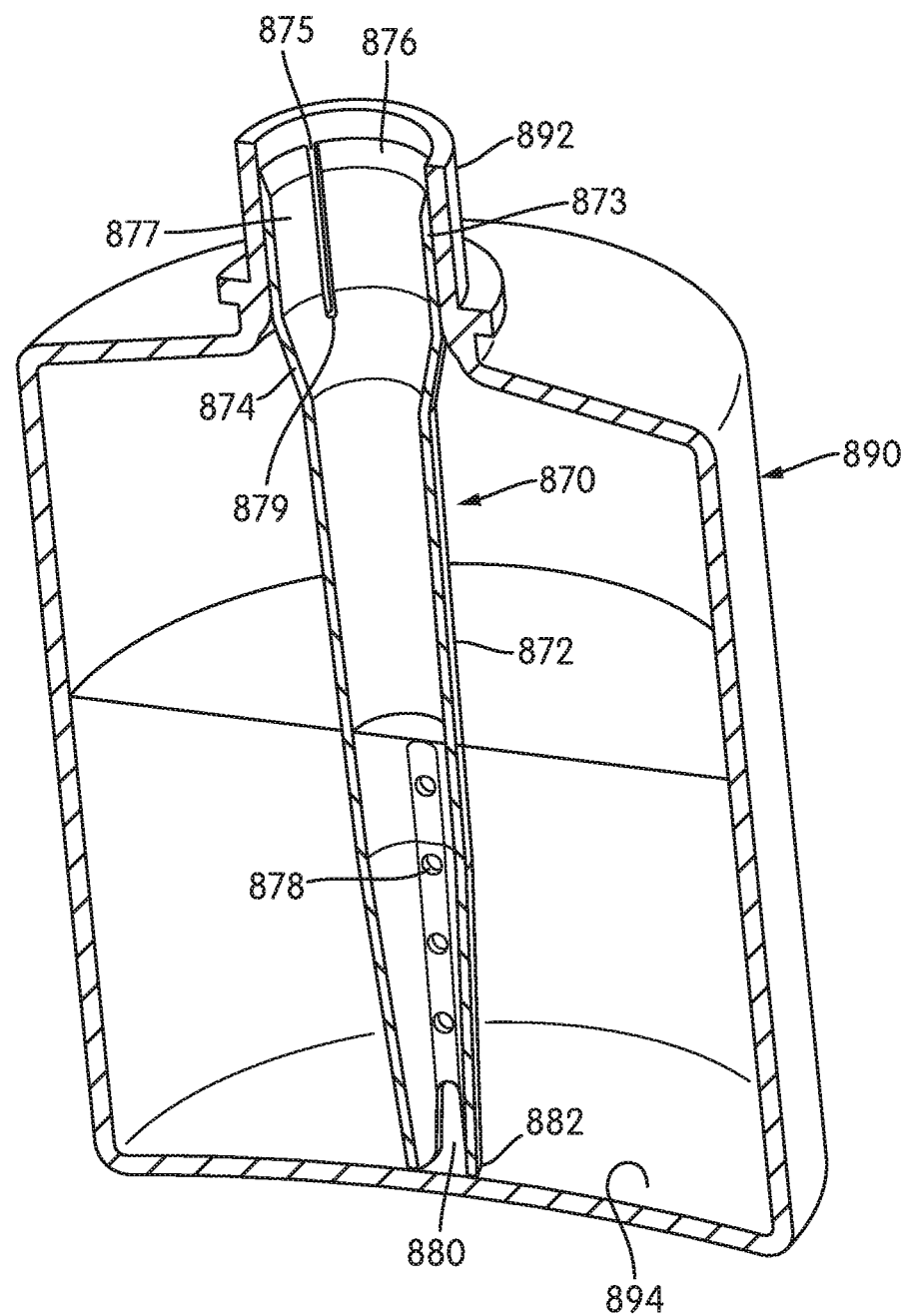
FIG. 17 is a cross-sectional, perspective view of an alternate embodiment the container insert inserted into a container.

As noted above, a further alternate embodiment of a container insert for reducing the amount of evaporation from a container is indicated by reference number 870 in FIG. 17, which is a cross-sectional, perspective view of the container insert 870 inserted into a container 890. The container insert 870 includes a body 872 with a plurality of holes 878 formed in a side wall of the body 872. In various embodiments, the body 872 is tapered with a decreasing dimension, e.g., diameter if circular in cross-section, from the top of the body 872 toward the bottom of the body 872.

The tapered shape of the embodiment of FIG. 17 is intended to generally conform to the shape of a pipette tip. This design should further limit evaporation because as a fluid is withdrawn from the container 890 (and the corresponding container insert 870), the fluid level drops and the surface area of the fluid exposed to the atmosphere becomes increasingly smaller. In some applications, however, the potential benefits of tapering to reduce evaporation must be balanced with the need to prevent contact between the container insert and a pipette tip inserted into the container insert. If pipettor-based level sensing is employed, contact between the pipette tip and the container insert could signal an incorrect position of the fluid surface and an associated analyzer could prematurely initiate an aspiration step before the pipette tip has actually contacted the fluid surface.

In an embodiment, the holes 878 may be longitudinally aligned along the body 872 and may be provided on one or more sides of the body 872. In various embodiments, a majority of the holes 878 are located in a lower portion of the body 872, meaning that all or most holes 878 are located in a lower half of the body 872. In various embodiments, there are at least three holes 878 on each of two opposed sides of the container insert 870, and there may be 4, 5, 6 or more holes 878 on each of two opposed sides of the insert 870 in such embodiments. In some embodiments, the container insert 870 includes a beveled surface 876 surrounding a top opening. In one or more embodiments, the container insert 870 includes one or more axial slots 880 extending from a bottom edge 882 of the body 872. In an embodiment, the container insert 870 includes two diametrically-opposed axial slots 880. As an alternative to the axial slots 880, the container insert 870 may have an irregular or undulating bottom edge.

In an exemplary embodiment, the container insert 870 includes, above the body 872, an upper portion 873 of a transverse dimension, e.g., a diameter that is larger than a transverse dimension of the body 872 and a tapered transition 873 between the upper portion 873 and the body 872.

The container insert 870 is inserted into the container 890 through an opening at the top of a neck 892 of the container 890. As shown in FIG. 17, the length of the container insert 870 may be such that a top end of the insert 870 is disposed at or just below the top of the container neck 892 and the bottom edge 882 of the insert 870 is in contact with the bottom 894 of the container 890. The axial slot(s) 880 of the container insert 870 prevent the bottom edge 882 from forming a sealing contact with the bottom 894 of the container 890.

In various embodiments, an insert retainer feature of the container insert 870 includes a number of resilient tabs 877 (e.g., two or more) defined by angularly-spaced, axial slits 875 extending from a top edge of the insert 870. The tabs 877 may be splayed radially outwardly—when the container insert 870 is not installed in a container—so that the outer width (e.g., diameter) of the upper portion 873 in the vicinity of the tabs 877 is larger than the inside width of the container opening. The tabs 877 thus flex radially inwardly as the container insert 870 is fully inserted into the container opening, and the resilience of the tabs 877 generates a radial force between the tabs 877 and the inside of the container opening, thereby securing the insert 870 within the container 890.

In various embodiments, when the container insert 870 is fully inserted into a container 890, the lower end of each slit 875 separating a pair of tabs 877 extends below the neck 892 of the container 890, thereby creating a small vent 879 near the neck of the container to prevent a vacuum from forming in the container and to permit air to escape from the container 890 during fluid fill.

As with container inserts 820 and 850 described above, the holes 878 formed in the body 872 of the insert 870 allow fluid within the container—including particles or beads in suspension—to flow between the space inside the body 872 and the space outside the body 872. Moreover, the slot(s) 880 allow fluid within the container 890 to mix and to enter the container insert 870 through the slot(s) 880. The size and number of slot(s) 880 at the base of the insert are chosen to facilitate fluid flow into and out of the body 872 and removal of fluid from the container by a fluid transfer apparatus, such as a robotic pipettor, inserted into the body 872. In one embodiment, the slot(s) are approximately 5/16 inches in length. These slot(s) may be flared out as shown, meaning that the slot is wider at one end—e.g., the lower end—than at an opposite end—e.g., the top end.

The material selected for the container insert should not leach when contacted with the fluid to be contained. In various embodiments, the container insert is injection molded with the same material used to form the container (e.g., polyethylene or polypropylene).

Comparative Data

Representative data indicative of the efficacy of a fluid container mixing device embodying aspects of the present disclosure is shown in TABLE 1 below.

TABLE 1

|  | Absorption (600 nm) | % of Panther |
|---|---|---|
| AC2 |  |  |
| AC2 250TK mixed on Panther | 0.3312 | 100.0% |
| AC2 250TK 3.75 Hz 20 sec | 0.320 | 96.5% |
| AC2 250TK 3.75 Hz 10 min | 0.336 | 101.3% |
| AC2 100TK 3.75 Hz 10 min | 0.335 | 101.2% |
| Ultrio |  |  |
| Ultrio mixed on Panther | 0.5132 | 100.0% |
| Ultrio 3.75 Hz 20 sec | 0.505 | 98.4% |
| Ultrio 3.75 Hz 10 min | 0.513 | 100.0% |

Each AC2 sample contains 100 µL, TCR and 900 µL, swab transport medium ("STM") Each Ultrio sample contains 400 µL, TCR and 600 µL, STM In TABLE 1, mixing data for two different types of target capture reagent ("TCR"), "AC2" and "Ultrio", is shown for differently-sized containers and different mixing conditions.

Since light passed through a fluid is partially absorbed by particles suspended in the fluid, the more particles that are suspended in the fluid the more light that is absorbed. Thus, the level of light absorption is an indication of the amount of particles suspended in the fluid and thus how "mixed-up" the fluid is. Thus, mixing efficacy is inferred, in the data presented in TABLE 1, from the level of absorption of 600 nm light passed through an aliquot of fluid taken from near the top of the fluid surface within the container and measured with a spectrophotometer. The amount of mixing—as inferred from the amount of absorption-achieved by a fluid container mixing device embodying aspects of the present disclosure is compared against the amount of mixing achieved by the TCR mixer employed in the "PANTHER" molecular diagnostic system available from Hologic, Inc. (see U.S. Pat. No. 7,135,145 "Device for agitating the fluid contents of a container").

For the AC2 TCR, mixing achieved in differently-sized containers—250 test kit ("TK") medium container or 100 TK small container—mixed at 3.75 Hz for 20 seconds or 10 minutes was compared to mixing achieved in a 250 TK container mixed on the PANTHER TCR mixer. The mixing achieved by the PANTHER TCR mixer resulted in a level of absorption of 0.3312. The mixing achieved by the mixing device of the present disclosure resulted in a level of absorption of 0.320 when a 250 TK container was mixed for 20 seconds, 0.336 when a 250 TK container was mixed for 10 minutes, and 0.335 when a 100 TK container was mixed for 10 minutes. Thus, after 20 seconds, the mixing device of the present disclosure achieved 96.5% of the level of mixing that was achieved by the PANTHER TCR mixer, and after 10 minutes, the mixing device of the present disclosure achieved more than 101% of the level of mixing that was achieved by the PANTHER TCR mixer.

For the Ultrio TCR, mixing achieved in a large container at 3.75 Hz for 20 seconds or 10 minutes was compared to mixing achieved by the PANTHER TCR mixer. The mixing achieved by the PANTHER TCR mixer resulted in a level of absorption of 0.5132. The mixing achieved by the mixing device of the present disclosure resulted in a level of absorption of 0.505 when the suspension was mixed for 20 seconds and 0.513 when the suspension was mixed for 10 minutes. Thus, after 20 seconds, the mixing device of the present disclosure achieved 98.4% of the level of mixing that was achieved by the PANTHER TCR mixer, and after 10 minutes, the mixing device of the present disclosure achieved 100% of the level of mixing that was achieved by the PANTHER TCR mixer.

Thus, the data of TABLE 1 demonstrates that a fluid container mixing device embodying aspects of the present disclosure achieves a level of mixing that is as good as or better than the level of mixing achieved by the PANTHER TCR mixer.

Hardware and Software

Aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as keyboards, touch screens, microphones, switches, manually-operated scanners, etc. Data output components may comprise hard drives or other storage media, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the apparatus has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the apparatus requires features or combinations of features other than those expressly recited in the claims. Accordingly, the disclosure is deemed to include all modifications and variations encompassed within the spirit and scope of the following appended claims.

The invention claimed is:

1. A method for mixing the fluid contents of a container while retarding evaporation of the fluid contents from the container, the method comprising:
   inserting a single-piece evaporation-limiting insert into an opening of a neck of the container, the evaporation-limiting insert comprising a hollow tubular body configured to extend into the container from the neck of the container, the tubular body including a plurality of holes formed through a wall of the tubular body and distributed along at least a portion of the length of the tubular body, and wherein the fluid contents comprise solid supports, wherein each of the holes is sized to permit passage of the solid supports therethrough, and wherein agitating the fluid contents of the container is performed to keep the solid supports in suspension; and
   agitating the fluid contents of the container to promote mixing of the fluid contents, whereby the holes formed through the wall of the tubular body of the insert permit fluid to flow through a space inside the tubular body.

2. The method of claim 1, wherein agitating the fluid contents of the container comprises agitating the container.

3. The method of claim 1, wherein the surface of the fluid contents within the container is above the top-most one of the holes formed through the wall of the tubular body.

4. The method of claim 1, further comprising the step of withdrawing a portion of the fluid contents from the container with a fluid transfer device inserted through the opening of the container and into the tubular body of the evaporation-limiting insert.

5. The method of claim 1, further comprising the step of determining the height of the fluid contents within the container with an apparatus configured to detect a fluid surface inserted through the opening of the container and into the tubular body of the evaporation-limiting insert.

6. The method of claim 1, wherein a majority of the holes are located on a lower portion of the tubular body.

7. The method of claim 6, wherein the solid supports are magnetically-responsive particles or beads.

8. The method of claim 1, wherein the tubular body has a length extending from the opening of the container to a bottom surface of the interior of the container, and wherein the tubular body has a bottom edge configured to form one or more gaps between the bottom edge and the bottom surface of the container.

9. The method of claim 8, wherein the bottom edge is an undulating surface such that one or more gaps are formed between the bottom edge and the bottom surface of the container.

10. The method of claim 8, wherein the tubular body of the evaporation-limiting insert comprises one or more slots extending axially from the bottom edge to thereby form one or more gaps between the bottom edge and the bottom surface of the container.

11. The method of claim 1, wherein the evaporation-limiting insert further comprises a retainer feature at the upper end portion of the tubular body that is configured to engage a portion of the container to secure the insert within the container.

12. The method of claim 11, wherein the retainer feature comprises a detent engaged with an inside surface of the container.

13. The method of claim 11, wherein the retainer feature comprises two or more outwardly splayed resilient tabs formed at a top portion of the tubular body and pressing resiliently against an inside surface of the container.

14. The method of claim 13, wherein the tabs are separated by slits extending lengthwise in a wall of the tubular body from a top edge thereof, wherein the length of each slit is longer than a neck of the container, so that the slit extends below the neck of the container.

15. The method of claim 1, wherein the holes through the evaporation-limiting insert are aligned axially along a side of the tubular body.

16. The method of claim 15, wherein the holes are arranged in two groups aligned axially along opposed sides of the tubular body.

17. The method of claim 1, wherein the tubular body is substantially cylindrical and has a substantially constant diameter along its entire length.

18. The method of claim 1, wherein the tubular body is tapered such that an outside dimension of the tubular body progressively decreases moving away from the opening of the container.

* * * * *